(12) United States Patent
Fishler et al.

(10) Patent No.: US 11,918,817 B2
(45) Date of Patent: Mar. 5, 2024

(54) REMOTE FOLLOW-UP METHODS, SYSTEMS, AND DEVICES FOR LEADLESS PACEMAKER SYSTEMS

(71) Applicant: Pacesetter, Inc., Sylmar, CA (US)

(72) Inventors: Matthew G. Fishler, Scotts Valley, CA (US); Suresh Gurunathan, Palo Alto, CA (US); Benjamin T. Persson, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 166 days.

(21) Appl. No.: 17/222,242

(22) Filed: Apr. 5, 2021

(65) Prior Publication Data

US 2021/0308470 A1 Oct. 7, 2021

Related U.S. Application Data

(60) Provisional application No. 63/033,737, filed on Jun. 2, 2020, provisional application No. 63/005,628, filed on Apr. 6, 2020.

(51) Int. Cl.
*A61N 1/372* (2006.01)
*A61N 1/05* (2006.01)
(Continued)

(52) U.S. Cl.
CPC ......... *A61N 1/37252* (2013.01); *A61N 1/056* (2013.01); *A61N 1/3702* (2013.01);
(Continued)

(58) Field of Classification Search
CPC .. A61N 1/37252; A61N 1/056; A61N 1/3702; A61N 1/3706; A61N 1/37223;
(Continued)

(56) References Cited

U.S. PATENT DOCUMENTS 9,168,383 B2 * 10/2015 Jacobson ........... A61N 1/37217
9,592,393 B2 3/2017 Stahmann et al.
(Continued)

OTHER PUBLICATIONS

Non-Final Office Action dated May 23, 2023, U.S. Appl. No. 17/222,279.
(Continued)

*Primary Examiner* — Brian T Gedeon
(74) *Attorney, Agent, or Firm* — Vierra Magen Marcus LLP

(57) ABSTRACT

Described herein are methods, devices, and systems for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses. Such a method can include the LP monitoring for a presence of one or more notification conditions associated with the LP and/or associated with a patient within which the LP is implanted, and the LP periodically outputting an advertisement sequence of pulses, using at least implantable electrodes of the LP, irrespective of whether the LP recognizes the presence of at least one notification condition. The method can also include the LP recognizing the presence of at least one notification condition, and based thereon, the LP also outputting a notification sequence of pulses.

19 Claims, 19 Drawing Sheets

(51) Int. Cl.
    *A61N 1/37*      (2006.01)
    *A61N 1/375*      (2006.01)
    *H04B 13/00*      (2006.01)
    *H04W 76/10*      (2018.01)

(52) U.S. Cl.
    CPC ....... *A61N 1/3706* (2013.01); *A61N 1/37223* (2013.01); *A61N 1/37258* (2013.01); *A61N 1/37512* (2017.08); *A61N 1/3756* (2013.01); *H04B 13/005* (2013.01); *H04W 76/10* (2018.02); *A61N 1/3727* (2013.01)

(58) Field of Classification Search
    CPC ............ A61N 1/37258; A61N 1/37512; A61N 1/3756; A61N 1/3727; A61N 1/37247; A61N 1/37235; H04B 13/005; H04W 76/10
    See application file for complete search history.

(56) References Cited

U.S. PATENT DOCUMENTS

| | | |
|---|---|---|
| 2011/0301435 A1 | 12/2011 | Albert et al. |
| 2014/0221859 A1 | 8/2014 | Albert |
| 2015/0174414 A1 | 6/2015 | Stahmann et al. |
| 2016/0059007 A1 | 3/2016 | Koop |
| 2016/0121128 A1 | 5/2016 | Fishler et al. |
| 2016/0206892 A1 | 7/2016 | Demmer |
| 2018/0021583 A1 | 1/2018 | Ciciarelli et al. |
| 2018/0035920 A1 | 2/2018 | Gunderson et al. |
| 2018/0056075 A1 | 3/2018 | Hahn et al. |
| 2018/0078777 A1* | 3/2018 | Wu ................... A61N 1/37252 |
| 2018/0140853 A1 | 5/2018 | Maile et al. |
| 2018/0200525 A1* | 7/2018 | Schilling ............ A61N 1/37276 |
| 2018/0207433 A1 | 7/2018 | Koop et al. |
| 2019/0201701 A1 | 7/2019 | Balczewski et al. |

OTHER PUBLICATIONS

U.S. Appl. No. 17/587,456, filed Jan. 28, 2022.
Extended European Search Report dated Jul. 18, 2022, European Patent Application No. 22155857.0-1126.
Restriction Requirement dated Dec. 29, 2022, U.S. Appl. No. 17/222,279, filed Apr. 5, 2021.
Response to Office Action dated Jan. 20, 2023, European Patent Application No. 22155857.0-1126.
Response to Restriction Requirement dated Feb. 10, 2023, U.S. Appl. No. 17/222,279, filed Apr. 5, 2021.
U.S. Appl. No. 17/222,279, filed Apr. 5, 2021.
U.S. Appl. No. 17/701,132 filed Mar. 22, 2022.
Response to Office Action dated Aug. 1, 2023, U.S. Appl. No. 17/222,279.

* cited by examiner

REMOTE FOLLOW-UP METHODS, SYSTEMS, AND DEVICES FOR LEADLESS PACEMAKER SYSTEMS

PRIORITY CLAIM

This application claims priority to U.S. Provisional Patent Application No. 63/005,628, filed Apr. 6, 2020, and U.S. Provisional Patent Application No. 63/033,737, filed Jun. 2, 2020, each of which is incorporated herein by reference.

RELATED APPLICATION

This application is related to commonly invented and commonly assigned U.S. patent application Ser. No. 17/222,279, filed the same day as the present application.

FIELD OF TECHNOLOGY

Embodiments described herein generally relate to methods, systems and devices that can be used to provide remote follow-up capabilities and solutions for use with one or more leadless pacemakers implanted within a patient.

BACKGROUND

An implantable medical device (IMD), such as a leadless pacemaker (LP), needs to communicate with a non-implanted device from time to time so that the non-implanted device can, e.g., program the implantable device, interrogate the implantable device, and/or obtain notifications and/or other types of diagnostic information from the implantable device. Typically, an LP is only capable of communicating with a non-implanted programmer that is operated by medical personnel, such as a physician or clinician. Accordingly, it is typically the case than an LP can only communicate with a non-implanted device when the patient visits a medical office that owns or otherwise has access to a non-implanted programmer, which can also be referred to an external programmer, or more succinctly as a programmer.

Communication between an LP and a non-implanted programmer may be facilitated by conductive communication via patient tissue. The use of conductive communication of information provides certain improvements over more conventional radio frequency (RF) and inductive communication techniques. For example, conductive communication techniques enable communication without requiring a programmer head be held close to a patient or to be held in a precise position relative to an implant site for an extended period of time. Conductive communication also enables power consumption to be reduced due to substantially lower current requirements and eliminating peak power demands currently imposed by existing inductive and RF communication techniques. This can beneficially extend the life of an LP. Also, conductive communication techniques use elements generally already existing in an LP, such as the therapeutic electrodes that function as an input-output device, enabling elimination of a coil or an antenna that are conventionally used for inductive and RF communication and reducing complexity and component count significantly.

In order to perform conductive communication, at least two programmer skin electrodes (that are part of or coupled to a non-implanted programmer) are attached to skin of a patient within which (i.e., in whom) one or more LPs is/are implanted, and the programmer skin electrodes are used to transmit information to and/or receive information from the LP(s) via conduction through body tissue of the patient. One potential problem with using conductive communication is that the orientation of the LP(s) can cause fading that can adversely affect both programmer-to-implant (p2i) communication and implant-to-programmer (i2p) communication. More specifically, certain orientations of an LP may cause conductive communication to be intermittent or stop completely, which may occur when an electric potential field generated between programmer skin electrodes has too small a difference between the electrodes of the LP. Despite its limitations, the use of conductive communication to facilitate communication between a non-implanted programmer on one or more LPs has proved to be practical and is often used.

In order for an LP to be interrogated by or otherwise communicate with a non-implanted programmer, a patient (within which the LP is implanted) needs to visit a medical facility that has a non-implanted programmer, as mentioned above. This is time consuming for both the patient and the medical personnel, as well as costly to the patient in terms of increasing their medical bills. It would be beneficial if an LP can be interrogated from time to time without requiring the use of a non-implanted programmer and without requiring that a patient visit a medical facility.

SUMMARY

Certain embodiments of the present technology are directed to methods for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses. Such a method can include the LP monitoring for a presence of one or more notification conditions associated with the LP and/or associated with a patient within which the LP is implanted, and the LP periodically outputting an advertisement sequence of pulses, using at least two of the two or more implantable electrodes of the LP, irrespective of whether the LP recognizes the presence of at least one notification condition. The method can also include the LP recognizing the presence of at least one notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted. In accordance with certain embodiments, the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP.

In accordance with certain embodiments, the LP outputs the advertisement sequence of pulses, using at least two of the two or more implantable electrodes, during a cardiac refractory period once every Nth cardiac cycle of the patient within which the LP is implanted, wherein N is an integer that is greater than 1.

In accordance with certain embodiments, a method also includes the LP monitoring for a programmer acknowledgement sequence of pulses within a programmer acknowledgement monitor window following each outputting by the LP of the advertisement sequence of pulses, to thereby enable the LP to determine whether an external programmer is attempting to establish a communication session with the LP. In such an embodiment, response to the LP detecting the programmer acknowledgement sequence of pulses within the programmer acknowledgement monitor window, the LP cooperates with the external programmer to establish a communication session with the external programmer. During an established communication session with the external programmer, the LP abstains from outputting the notification sequence of pulses that is capable of being received by an external device that is incapable of programming the LP or by another IMD.

In accordance with certain embodiments, in response to the LP not detecting the programmer acknowledgement sequence of pulses within the programmer acknowledgement monitor window, the LP outputs the notification sequence of pulses within one or more notification transmission window(s) following the outputting of the advertisement sequence of pulses, wherein the notification transmission window follows the programmer acknowledgement monitor window. In accordance with certain such embodiments, when the LP does not detect the programmer acknowledgement within the programmer acknowledgement monitor window that follows the LP outputting the advertising sequence of pulses, the LP outputs the notification sequence of pulses within one or more notification transmission window(s) following the outputting of the advertisement sequence of pulses only if the LP has recognized the presence of at least one notification condition.

In accordance with certain embodiments, an external device monitors for the advertisement sequence of pulses (while at least two external electrodes of the external device, or communicatively coupled to the external device, are in contact with the patient within which the LP is implanted), or another IMD (e.g., an implantable cardiac monitor (ICM)) monitors for the advertisement sequence of pulses. A method can include the external device or other IMD detecting the advertisement sequence of pulses and in response thereto the external device or other IMD monitoring for the notification sequence of pulses within a respective notification monitor window following the advertisement sequence of pulses that was detected by the external device. The method can also include the external device or other IMD detecting the notification sequence of pulses within the respective notification monitor window following the advertisement sequence of pulses that was detected by the external device, and in response thereto, the external device or other IMD storing and/or transmitting to a patient care network, raw data associated with the notification sequence of pulses and/or information decoded from the notification sequence of pulses.

In accordance with certain embodiments, a method can include the external device or other IMD monitoring for the advertisement sequence of pulses, and the external device or other IMD detecting the advertisement sequence of pulses and in response thereto the external device or other IMD monitoring for the notification sequence of pulses within a respective notification monitor window following the advertisement sequence of pulses that was detected by the external device or other IMD. If the external device or other IMD does not detect the notification sequence of pulses within the respective notification monitor window following the advertisement sequence of pulses that was detected by the external device, then in response thereto, the external device or other IMD stores and/or transmits to a patient care network an indication that no notification condition was reported by the LP.

In accordance with certain embodiments, the external device or other IMD does not output any pulses or other signals that are detectable by the LP implanted within the patient, and thus, the LP is unaware of whether any instances of the advertisement sequence of pulses and the notification sequence of pulses that the LP outputs are received by the external device or other IMD.

In accordance with certain embodiments, the LP monitors for an external device acknowledgement sequence of pulses within an external device acknowledgement monitor window that precedes, at least partially overlaps with, or follows the programmer acknowledgement monitor window. In response to the LP detecting the external device acknowledgement sequence of pulses within the external device acknowledgement monitor window, the LP outputs the notification sequence of pulses within one or more notification transmission windows following the outputting of the advertisement sequence of pulses, wherein the notification transmission window follows both the programmer acknowledgement monitor window and the external device acknowledgement monitor window. In accordance with certain embodiments, the LP outputs the notification sequence of pulses within one or more of the notification transmission window(s) following the outputting of the advertisement sequence of pulses only if the LP has recognized the presence of at least one notification condition and the LP has detected the external device acknowledgement sequence of pulses within the external device acknowledgement monitor window. In accordance with certain embodiments, the LP limits how often the LP outputs the notification sequence of pulses within a specified period of time in order to conserve power of the LP.

In accordance with certain embodiments, the LP outputs a portion of the notification sequence of pulses irrespective of whether LP detects the external device acknowledgement sequence of pulses within the external device acknowledgment window. In certain such embodiments, the LP outputs a further portion of the notification sequence of pulses (over one or more frames over one or more cardiac cycles) in response to the LP detecting the external device acknowledgement sequence of pulses within the external device acknowledgment window.

In accordance with certain embodiments, the one or more notification conditions that the LP monitors for includes at least one notification condition associated with the LP and/and at least one notification condition associated with the patient within which the LP is implanted. In accordance with certain embodiments, the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition. In accordance with certain embodiments, the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

Certain embodiments of the present technology are directed to an implantable LP, comprising a pulse generator, two or more electrodes, and a controller. The pulse generator is configured to selectively produce conductive communication pulses. The two or more electrodes are coupled to the pulse generator and used to output the conductive communication pulses produced by the pulse generator. The controller is configured to monitor for a presence of one or more notification conditions associated with the LP and/or associated with a patient within which the LP is implanted. Additionally, the controller is configured to periodically cause an advertisement sequence of the conductive communication pulses to be produced by the pulse generator, so that the advertisement sequence is output using at least two of the two or more electrodes, irrespective of whether of the presence of at least one notification condition. The controller is also configured to cause a notification sequence of the conductive communication pulses to be produced by the pulse generator, so that the notification sequence is output using at least two of the two or more implanted electrodes, in response to the presence of at least one notification condition being detected.

In accordance with certain embodiments, the controller of the LP is configured to cause the advertisement sequence of the conductive communication pulses to be produced by the pulse generator, so that the advertisement sequence is output using at least two of the two or more electrodes, during a cardiac refractory period once every Nth cardiac cycle of the patient within which the LP is implanted, wherein N is an integer that is greater than 1.

In accordance with certain embodiments, the controller of the LP is configured to: monitor for a programmer acknowledgement sequence of pulses within a programmer acknowledgement monitor window following each outputting of the advertisement sequence of pulses, to thereby enable the controller to determine whether an external programmer is attempting to establish a communication session with the LP. The controller is also configured to cooperate with an external programmer to establish a communication session therewith in response to the programmer acknowledgement sequence of pulses being detected within the programmer acknowledgement monitor window.

In accordance with certain embodiments, the controller of the LP is configured to: monitor for a programmer acknowledgement sequence of pulses within a programmer acknowledgement monitor window following each output of the advertisement sequence of pulses, to thereby enable the controller to determine whether an external programmer is attempting to establish a communication session with the LP, and cause the notification sequence of the conductive communication pulses to be produced by the pulse generator within a notification transmission window following the advertisement sequence of pulses, in response to the controller not detecting the programmer acknowledgement sequence of pulses within the programmer acknowledgement monitor window. In certain such embodiments, the controller of the LP is configured to cause the notification sequence of the conductive communication pulses to be generated and output only if the controller has recognized the presence of at least one notification condition.

In accordance with certain embodiments, the controller of the LP is configured to monitor for a programmer acknowledgement sequence of pulses within a programmer acknowledgement monitor window following each outputting by the LP of the advertisement sequence of pulses, to thereby enable the controller to determine whether an external programmer is attempting to establish a communication session with the LP. Additionally, the controller of the LP is configured to monitor for an external device acknowledgement sequence of pulses within an external device acknowledgement monitor window that precedes, at least partially overlaps with, or follows the programmer acknowledgement monitor window, in response to the controller not detecting the programmer acknowledgement sequence of pulses within the programmer acknowledgement monitor window. The controller of the LP is also configured to cause a notification sequence of the conductive communication pulses to be produced by the pulse generator, so that the notification sequence is output using at least two of the two or more electrodes of the LP, in response to the controller detecting the external device acknowledgement sequence of pulses within the external device acknowledgement monitor window. In certain such embodiments, the controller of the LP is configured to cause the notification sequence of the conductive communication pulses to be produced by the pulse generator, so that the notification sequence is output using at least two of the two or more implanted electrodes, only if the controller has recognized the presence of at least one notification condition and the controller has detected the external device acknowledgement sequence of pulses within the external device acknowledgement monitor window.

In accordance with certain embodiments, the controller of the LP is configured to limit how often the LP outputs the notification sequence of pulses within a specified period of time in order to conserve power of the LP.

In accordance with certain embodiments, the controller of the LP is configured to cause a portion of the notification sequence of the conductive communication pulses to be produced by the pulse generator, so that the portion of the notification sequence is output using at least two of the two or more electrodes of the LP, irrespective of whether LP detects the external device acknowledgement sequence of pulses within the external device acknowledgment window. The controller of the LP is also configured to cause a further portion of the notification sequence of the conductive communication pulses to be produced by the pulse generator, so that the further portion of the notification sequence is output using at least two of the two or more electrodes of the LP, in response to the controller detecting the external device acknowledgement sequence of pulses within the external device acknowledgment window.

Certain embodiments of the present technology are directed to a system comprising an implantable LP and an external device that is incapable of programming the LP. The LP includes a pulse generator, two or more implantable electrodes, and a controller. The pulse generator of the LP is configured to selectively produce conductive communication pulses, and the two or more implantable electrodes of the LP are coupled to the pulse generator of the LP and used to output the conductive communication pulses produced by the pulse generator. The external device includes or is communicatively coupled to two or more external electrodes used to receive conductive communication pulses from the LP. The controller of the LP is configured to monitor for a presence of one or more notification conditions associated with the LP and/or associated with a patient within which the LP is implanted, and periodically cause an advertisement sequence of the conductive communication pulses to be produced by the pulse generator, so that the advertisement sequence is output using at least two of the two or more electrodes, irrespective of whether of the presence of at least one notification condition. The controller of the LP is also configured to cause a notification sequence of the conductive communication pulses to be produced by the pulse generator, so that the notification sequence is output using at least two of the two or more implanted electrodes, in response to the presence of at least one notification condition being detected. In accordance with certain such embodiments, the advertisement sequence of pulses and the notification sequence of pulses and/or information encoded therein are capable of being received by the external device that includes or is communicatively coupled to two or more external electrodes used to receive conductive communication pulses from the LP.

In accordance with certain embodiments, the LP outputs the advertisement sequence of pulses, using at least two of the two or more implantable electrodes, during a cardiac refractory period once every Nth cardiac cycle of the patient within which the LP is implanted, wherein N is an integer that is greater than 1.

In accordance with certain embodiments, the LP is configured to monitor for a programmer acknowledgement sequence of pulses within a programmer acknowledgement monitor window following each outputting by the LP of the advertisement sequence of pulses, to thereby enable the LP to determine whether an external programmer is attempting to establish a communication session with the LP. In response to the LP not detecting the programmer acknowledgement sequence of pulses within the programmer acknowledgement monitor window, the LP is configured to output the notification sequence of pulses within one or more notification transmission windows following the outputting of the advertisement sequence of pulses, wherein each notification transmission window precedes, at least partially overlaps with, or follows a respective programmer acknowledgement monitor window.

In accordance with certain embodiments, the external device is configured to monitor for the advertisement sequence of pulses while at least two of the two or more external electrodes of the external device or communicatively coupled to the external device are in contact with the patient within which the LP is implanted. The external device is also configured to detect the advertisement sequence of pulses and in response thereto monitor for a notification sequence of pulses within a respective notification monitor window following the advertisement sequence of pulses that was detected by the external device. The external device is also configured to detect the notification sequence of pulses within the respective notification monitor window following the advertisement sequence of pulses that was detected by the external device, and in response thereto, store within the external device and/or transmit to a patient care network, raw data associated with the notification sequence of pulses and/or information decoded from the notification sequence of pulses.

In accordance with certain embodiments, the external device is configured to monitor for the advertisement sequence of pulses while at least two of the two or more external electrodes of the external device or communicatively coupled to the external device are in contact with the patient within which the LP is implanted, and detect the advertisement sequence of pulses and in response thereto monitor for a notification sequence of pulses within a respective notification monitor window following the advertisement sequence of pulses that was detected by the external device. If the external device does not detect the notification sequence of pulses within the respective notification monitor window following the advertisement sequence of pulses that was detected by the external device, then in response thereto the external device can store within the external device and/or transmit to a patient care network an indication that no notification condition was reported by the LP.

In accordance with certain embodiments, the external device does not output any pulses or other signals that are detectable by the LP implanted within the patient, and thus, the LP is unaware of whether any instances of the advertisement sequence of pulses and the notification sequence of pulses that the LP outputs are received by the external device.

In accordance with certain embodiments, the LP is configured to monitor for a programmer acknowledgement sequence of pulses within a programmer acknowledgement monitor window following each outputting by the LP of the advertisement sequence of pulses, to thereby enable the LP to determine whether an external programmer is attempting to establish a communication session with the LP. The LP is also configured to monitor for an external device acknowledgement sequence of pulses within an external device acknowledgement monitor window that precedes, at least partially overlaps with, or follows the programmer acknowledgement monitor window; and in response to detecting the external device acknowledgement sequence of pulses within the external device acknowledgement monitor window, output the notification sequence of pulses within one or more notification transmission windows following the outputting of the advertisement sequence of pulses.

In accordance with certain embodiments, the LP is configured to output the notification sequence of pulses within one or more notification transmission windows following the outputting of the advertisement sequence of pulses only if the LP has recognized the presence of at least one notification condition and the LP has detected the external device acknowledgement sequence of pulses within the external device acknowledgement monitor window.

In accordance with certain embodiments, the LP is configured to limit how often the LP outputs the notification sequence of pulses within a specified period of time in order to conserve power of the LP.

In accordance with certain embodiments, the LP is configured to output a portion of the notification sequence of pulses irrespective of whether LP detects the external device acknowledgement sequence of pulses within the external device acknowledgment window, and output a further portion of the notification sequence of pulses in response to the LP detecting the external device acknowledgement sequence of pulses within the external device acknowledgment window.

Certain embodiments of the present technology are directed to methods for use with a system including an implantable LP with a remote follow-up capability whereby the LP can provide diagnostic information to an external device that is incapable of programming the LP, wherein the LP includes two or more implantable electrodes used to output both pacing pulses and conductive communication pulses, and wherein the external device includes or is communicatively coupled to first, second, and third external electrodes used to receive conductive communication pulses from the LP. Such a method can include the external device monitoring for an advertisement sequence of pulses while the first and second external electrodes, but not the third electrode, are in contact with the patient within which the LP is implanted. The method also includes the external device measuring a metric indicative of power and/or quality of a conductive communication signal received from the LP while the first and second external electrodes, but not the third electrode, are in contact with the patient within which the LP is implanted, the conductive communication signal including at least one instance of the advertisement sequence of pulses. In response to the metric being below a threshold level, the external device provides instructions for the patient to also contact the third electrode such that the patient will be in contact with the first, second and third electrodes at a same time.

In accordance with other embodiments, a method includes the external device monitoring for an advertisement sequence of pulses using first, second, and third subsets of the external electrodes, the first subset including the first and second external electrodes, the second subset including the first and third external electrodes, and the third subset including the second and third external electrodes. The method also includes the external device measuring for each subset of the external electrodes, of the first, second, and third subsets, a respective metric indicative of power and/or quality of a communication signal received from the LP using the subset of electrodes, and in dependence thereon, the external device identifying a preferred one of the first, second, and third subsets of the external electrodes. Additionally, the method includes the external device using the preferred one of the first, second, and third subsets of the external electrodes to receive the notification sequence of pulses from the LP, and the external device storing within the external device and/or transmitting to a patient care network, raw data associated with the notification sequence of pulses and/or information decoded from the notification sequence of pulses received from the LP using the preferred one of the first, second, and third subsets of the external electrodes.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology relate to methods, systems and devices that can be used to provide remote follow-up solutions and capabilities for use with one or more leadless cardiac pacemakers implanted within a patient. Before providing additional details of the specific embodiments of the present technology mentioned above, an example system in which embodiments of the present technology can be used will first be described with reference to FIGS. 1-3. More specifically, FIGS. 1-3 will be used to describe an example cardiac pacing system, wherein pacing and sensing operations can be performed by multiple medical devices, which may include one or more leadless cardiac pacemakers, an implantable cardioverter defibrillator (ICD), such as a subcutaneous-ICD, an implantable cardiac monitor (ICM) and/or a programmer to reliably and safely coordinate pacing and/or sensing operations. A leadless cardiac pacemaker can also be referred to more succinctly herein as a leadless pacemaker (LP).

Figure 1:
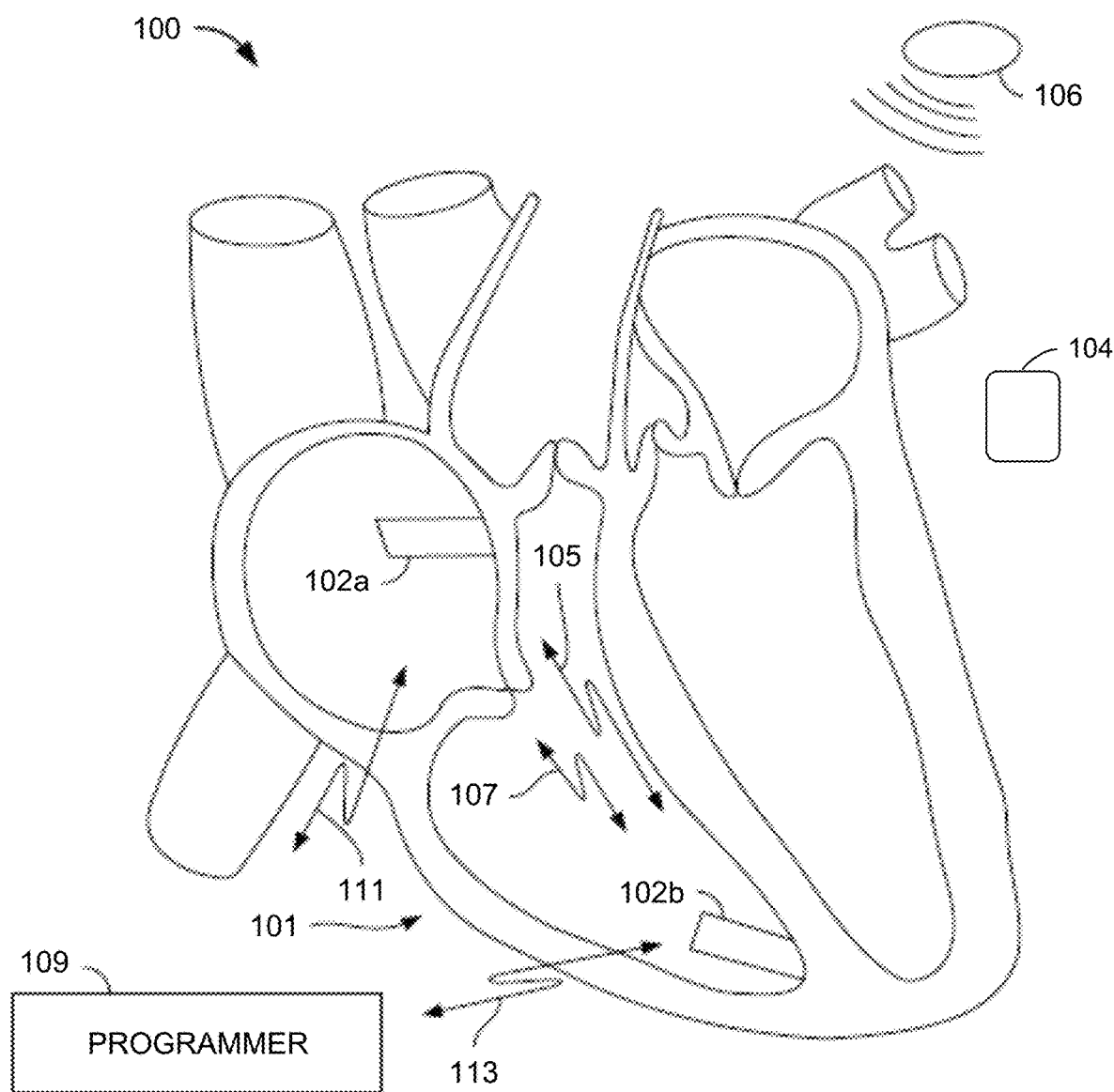
FIG. 1 illustrates a system formed in accordance with certain embodiments herein as implanted in a heart.

FIG. 1 illustrates a system 100 that is configured to be implanted in a heart 101. The system 100 includes two or more LPs 102a and 102b located in different chambers of the heart. LP 102a is located in a right atrium, while LP 102b is located in a right ventricle. LPs 102a and 102b communicate with one another to inform one another of various local physiologic activities, such as local intrinsic events, local paced events, and/or the like. LPs 102a and 102b may be constructed in a similar manner, but operate differently based upon which chamber LP 102a or 102b is located. The LPs 102a and 102b may sometimes be referred to collectively herein as the LPs 102, or individually as an LP 102.

In certain embodiments, LPs 102a and 102b communicate with one another, and/or with an ICM 104, and/or with an ICD 106, by conductive communication through the same electrodes that are used for sensing and/or delivery of pacing therapy. The LPs 102a and 102b may also be able to use conductive communication to communicate with a non-implanted device, e.g., an external programmer 109, having electrodes placed on the skin of a patient within which the LPs 102a and 102b are implanted. While not shown (and not preferred, since it would increase the size and power consumption of the LPs 102a and 102b), the LPs 102a and 102b can potentially include an antenna and/or telemetry coil that would enable them to communicate with one another, the ICD 106 and/or a non-implanted device using RF or inductive communication. While only two LPs are shown in FIG. 1, it is possible that more than two LPs can be implanted in a patient. For example, to provide for bi-ventricular pacing and/or cardiac resynchronization therapy (CRT), in addition to having LPs implanted in the right atrial (RA) chamber and the right ventricular (RV) chamber, a further LP can be implanted in the left ventricular (LV) chamber. It is also possible that a single LP be implanted within a patient, e.g., in the RV chamber, or the LV chamber, but not limited thereto.

In some embodiments, one or more LP 102a, 102b can be co-implanted with the ICM 104 and/or the ICD 106. Each LP 102a, 102b uses two or more electrodes located within, on, or within a few centimeters of the housing of the pacemaker, for pacing and sensing at the cardiac chamber, for bidirectional communication with one another, with the programmer 109, and/or the ICD 106. Such an ICM 104 can be intended for subcutaneous implantation at a site near the heart 101. The ICM 104 can include, for example, a pair of spaced-apart sense electrodes positioned with respect to a housing, wherein the sense electrodes provide for detection of far-field EGM signals, and can also be used for conductive communications with one or more other implanted devices, such as the LP(s) 102a and/or 102b and/or the ICD 106. Such an ICM can also include an antenna that is configured to wirelessly communicate with an external device, such as an external programmer 109, or a remote monitor (e.g., 702 described below with reference to FIGS. 7A and 7B), in accordance with one or more predetermined wireless protocols (e.g., Bluetooth, Bluetooth low energy, Wi-Fi, etc.). The housing of the ICM can include various other components such as: sense electronics for receiving signals from the electrodes, a microprocessor for processing the signals in accordance with algorithms, such as the AF detection algorithm described herein, a loop memory for temporary storage of cardiac activity (CA) data, a device memory for long-term storage of CA data upon certain triggering events, such as AF detection, sensors for detecting patient activity and a battery for powering components. In accordance with certain embodiments, the ICM 104 can act as a bridge communication device between the LPs 102a and/or 102b and an external programmer 109 and/or a remote monitor, as will be described in additional detail below.

Figure 2:
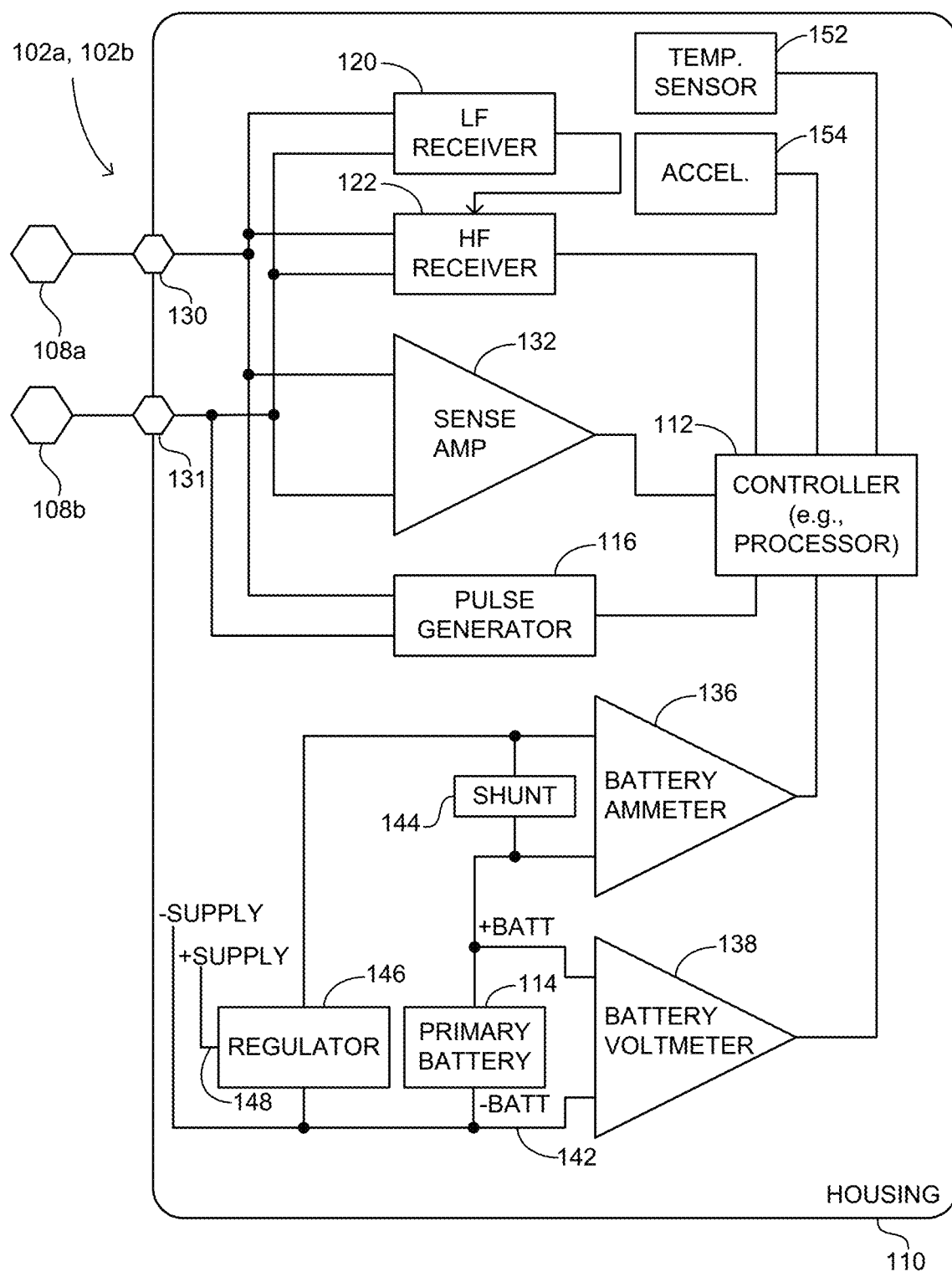
FIG. 2 is a block diagram of a single LP in accordance with certain embodiments herein.

Referring to FIG. 2, a block diagram shows an embodiment for portions of the electronics within LPs 102a, 102b configured to provide conductive communication through the same electrodes that are used for cardiac pacing and/or sensing. Each of the LPs 102a, 102b includes at least two leadless electrodes configured for delivering cardiac pacing pulses, sensing evoked and/or natural cardiac electrical signals, and unidirectional and/or bi-directional communication. In FIG. 2 (and FIG. 3) the two electrodes shown therein are labeled 108a and 108b. Such electrodes can be referred to collectively as the electrodes 108, or individually as an electrode 108. An LP 102, or other type of IMD, can include more than two electrodes 108, depending upon implementation.

In FIG. 2, each of the LPs 102a, 102b is shown as including first and second receivers 120 and 122 that collectively define separate first and second communication channels 105 and 107 (FIG. 1), (among other things) between LPs 102a and 102b. Although first and second receivers 120 and 122 are depicted, in other embodiments, each LP 102a, 102b may only include the first receiver 120, or may include additional receivers other than first and second receivers 120 and 122. As will be described in additional detail below, the pulse generator 116 can function as a transmitter that transmits conductive (e.g., i2i or i2p) communication signals using the electrodes 108. In certain embodiments, LPs 102a and 102b may communicate over more than just first and second communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses. Usage of the electrodes 108 for communication enables the one or more LPs 102a, 102b to perform antennaless and telemetry coil-less communication.

The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 100 kHz) and the receiver 122 is configured to monitor for one or more signals within a relatively high frequency range (e.g., above 100 kHz). In certain embodiments, the receiver 120 (and more specifically, at least a portion thereof) is always enabled and monitoring for a wakeup notice, which can simply be a wakeup pulse, within a specific low frequency range (e.g., between 1 kHz and 100 kHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. The low power receiver 120 is incapable of receiving signals within the relatively high frequency range (e.g., above 100 kHz), but consumes significantly less power than the high power receiver 122. This way the low power receiver 120 is capable of always monitoring for a wakeup notice without significantly depleting the battery (e.g., 114) of the LP. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective conductive (e.g., i2i) communication without unnecessarily and rapidly depleting the battery of the LP (which the high power receiver 122 may do if it were always enabled). Such a wakeup notice can be received, by the low power receiver 120, from another LP, an external programmer 109, or one of the remote monitors described herein, e.g., with reference to FIGS. 7 and 8, but not limited thereto.

In accordance with certain embodiments, when one of the LPs 102a and 102b senses an intrinsic event or delivers a paced event, the corresponding LP 102a, 102b transmits an implant event message to the other LP 102a, 102b. For example, when an atrial LP 102a senses/paces an atrial event, the atrial LP 102a transmits an implant event message including an event marker indicative of a nature of the event (e.g., intrinsic/sensed atrial event, paced atrial event). When a ventricular LP 102b senses or paces a ventricular event, the ventricular LP 102b transmits an implant event message including an event marker indicative of a nature of the event (e.g., intrinsic/sensed ventricular event, or paced ventricular event). In certain embodiments, each LP 102a, 102b transmits an implant event message to the other LP 102a, 102b preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice, wakeup pulse or wakeup signal) followed by an event marker. The notice trigger pulse (also referred to as the wakeup notice, wakeup pulse or wakeup signal) is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any conductive communication signal from another LP (or other IMD) or from a non-implanted device (e.g., a programmer 109) may transmit a receive acknowledgement indicating that the receiving LP (or other IMD, or non-implanted device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. Other variations are also possible and within the scope of the embodiments described herein. Each conductive communication signal can include one or more sequences of conductive communication pulses.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously.

For synchronous event signaling, LPs 102a and 102b may maintain synchronization and regularly communicate at a specific interval. Synchronous event signaling allows the transmitter and receivers in each LP 102a, 102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 µs, where the Tx/Rx time slots occur periodically (e.g., every 10-20 ms). Such time slots can also be referred to as windows.

LPs 102a and 102b may lose synchronization, even in a synchronous event signaling scheme. As explained herein, features may be included in LPs 102a and 102b to maintain device synchronization, and when synchronization is lost, LPs 102a and 102b undergo operations to recover synchronization. Also, synchronous event messages/signaling may introduce a delay between transmissions which causes a reaction lag at the receiving LP 102a, 102b. Accordingly, features may be implemented to account for the reaction lag.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of $\frac{1}{500}$ to $\frac{1}{10000}$. A gain factor may be $\frac{1}{1000}$th. Transmit current is a design factor in addition to receiver current. As an example, the system may allocate one-half of the implant communication current budget to the transmitter (e.g., 0.5 µA for each transmitter). When LP 102a, 102b maintains a transmitter in a continuous on-state and the electrode load is 500 ohms, a transmitted voltage may be 2.5V. When an event signal is transmitted at 2.5V, the event signal is attenuated as it propagates and would appear at LP 102a, 102b receiver as an amplitude of approximately 0.25 mV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

In accordance with certain embodiments herein, LPs 102a and 102b may utilize multi-stage receivers that implement a staged receiver wakeup scheme in order to improve reliability yet remain power efficient. Each of LPs 102a and 102b may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/ less than 10 µs per pulse) assigned to the second receive channel.

In accordance with certain embodiments, the first receiver 120 may maintain the first channel active (awake) at all times (including when the second channel is inactive (asleep)) in order to listen for messages from a remote LP. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP). The terms active, awake and enabled are used interchangeably herein.

Still referring to FIG. 2, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer 109 may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse-width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102a, 102b may implement an event message utilizing event signaling parameters for amplitude, pulse-width, pulse rate, etc. that correspond to a current draw of approximately 0.5 µA for transmit.

LP 102a, 102b may combine the event message transmissions with pacing pulses. For example, LP 102a, 102b may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102a or 102b senses an intrinsic event, it can send a qualitatively similar event pulse sequence (but indicative of a sensed event) without adding the pace pulse remainder. As LP 102a, 102b longevity calculations are designed based on the assumption that LP 102a, 102b will deliver pacing therapy 100% of the time, transmitting an intrinsic event marker to another LP 102a, 102b will not impact the nominal calculated LP longevity.

In some embodiments, LP 102a, 102b may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102a, 102b increases an extent to which LP 102a, 102b uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102a, 102b may use larger pulse-widths.

By combining event messages and low power pacing, LP 102a, 102b may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

While not shown, a communication capacitor can be provided in LP 102a, 102b. The communication capacitor may be used to transmit event signals having higher voltage for the event message pulses to improve communication, such as when the LPs 102a and 102b experience difficulty sensing event messages. The high voltage event signaling may be used for implants with high signal attenuation or in the case of a retry for an ARQ (automatic repeat request) handshaking scheme.

In some embodiments, the individual LP 102a can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP is communicating, the conductive communication may be unidirectional or bidirectional.

FIG. 2 depicts a single LP 102a (or 102b) and shows the LP's functional elements substantially enclosed in a hermetic housing 110. The LP 102a (or 102b) has at least two electrodes 108 located within, on, or near the housing 110, for delivering pacing pulses to and sensing electrical activity from the muscle of the cardiac chamber, and for conductive communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more leadless cardiac pacemakers 102a and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an ICD 106 in addition to one or more LPs 102a, 102b configured for implantation in electrical contact with a cardiac chamber and for performing cardiac rhythm management functions in combination with the implantable ICD 106. The implantable ICD 106 and the one or more LPs 102a, 102b configured for leadless intercommunication by information conduction through body tissue and/or wireless transmission between transmitters and receivers in accordance with the discussed herein.

In a further embodiment, a cardiac pacing system 100 comprises at least one LP 102a, 102b configured for implantation in electrical contact with a cardiac chamber and configured to perform cardiac pacing functions in combination with the co-implanted ICD 106. The leadless cardiac pacemaker or pacemakers 102a comprise at least two leadless electrodes 108 configured for delivering cardiac pacing pulses, sensing evoked and/or natural cardiac electrical signals, and transmitting information to the co-implanted ICD 106.

As shown in the illustrative embodiments, each LP pacemaker 102a, 102b can comprise two or more leadless electrodes 108 configured for delivering cardiac pacing pulses, sensing evoked and/or natural cardiac electrical signals, and bidirectionally communicating with one another and/or the co-implanted ICD 106.

LP 102a, 102b can be configured for operation in a particular location and a particular functionality at manufacture and/or at programming by an external programmer. Bidirectional communication among the multiple LPs can be arranged to communicate notification of a sensed heartbeat or delivered pacing pulse event and encoding type and location of the event to another implanted pacemaker or pacemakers. LP 102a, 102b receiving the communication decode the information and respond depending on location of the receiving pacemaker and predetermined system functionality.

In some embodiments, the LPs 102a and 102b are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

Referring to FIG. 2, the LP is shown as including a temperature sensor 152. The temperature sensor can be any one of various different types of well-known temperature sensors, or can be a future developed temperature sensor. For one example, the temperature sensor 152 can be a thermistor, a thermocouple, a resistance thermometer, or a silicon bandgap temperature sensor, but is not limited thereto. Regardless of how the temperature sensor 152 is implemented, it is preferably that the temperature sensed by the sensor is provided to the controller 112 as a digital signal indicative of the blood temperature of the patient within which the LP is implanted. The temperature sensor 152 can be hermetically sealed within the housing 110, but that need not be the case. The temperature sensor 152 can be used in various manners. For example, the temperature sensor 152 can be used to detect an activity level of the patient to adjust a pacing rate, i.e., for use in rate responsive pacing. When a person starts to exercise their core body temperature initially dips, and then after exercising for a prolonged period of time the person's core body temperature will eventually rise. Thereafter, when the person stops exercising their core body temperature will return to its baseline. Accordingly, the controller 112 can be configured to detect an activity level of a patient based on core blood temperature measurements obtained using the temperature sensor 152.

Referring to FIG. 2, the LP is also shown as including an accelerometer 154 which can be hermetically contained within the housing 110. The accelerometer 154 can be any one of various different types of well-known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. For example, the accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an (electrogram) EGM sensed using the electrodes 108, and/or sensed using a plethysmography signal obtained using a plethysmography sensor (not shown) or a heart sound sensor (not shown), but not limited thereto. One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain. The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
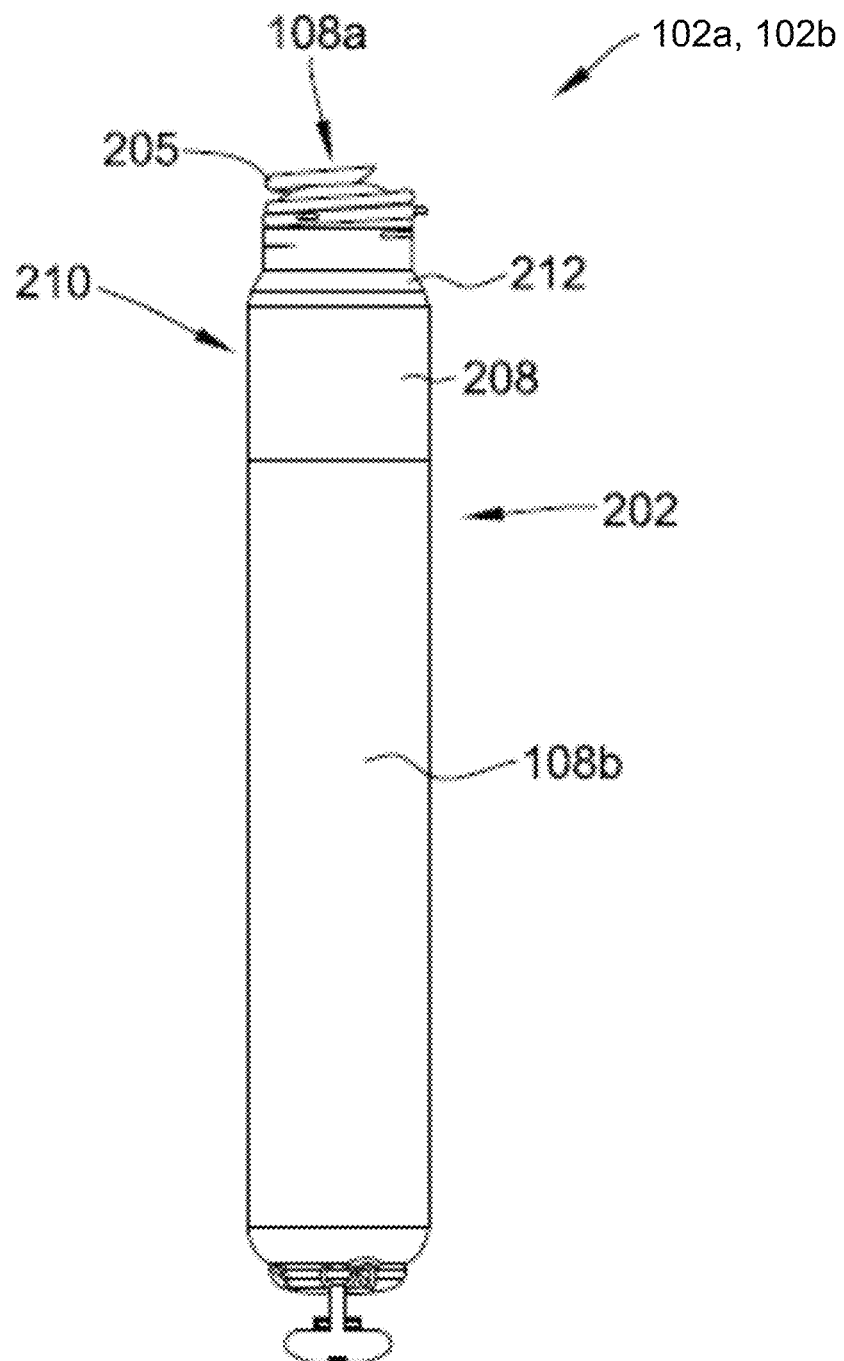
FIG. 3 illustrates an LP in accordance with certain embodiments herein.

FIG. 3 shows an LP 102a, 102b. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2.

The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102a and 102b can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, LP 102a and LP 102b operate as two independent leadless pacers maintaining beat-to-beat dual-chamber functionality via a "Master/Slave" operational configuration. For descriptive purposes, the ventricular LP 102b shall be referred to as "vLP" and the atrial LP 102a shall be referred to as "aLP". The LP 102a that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
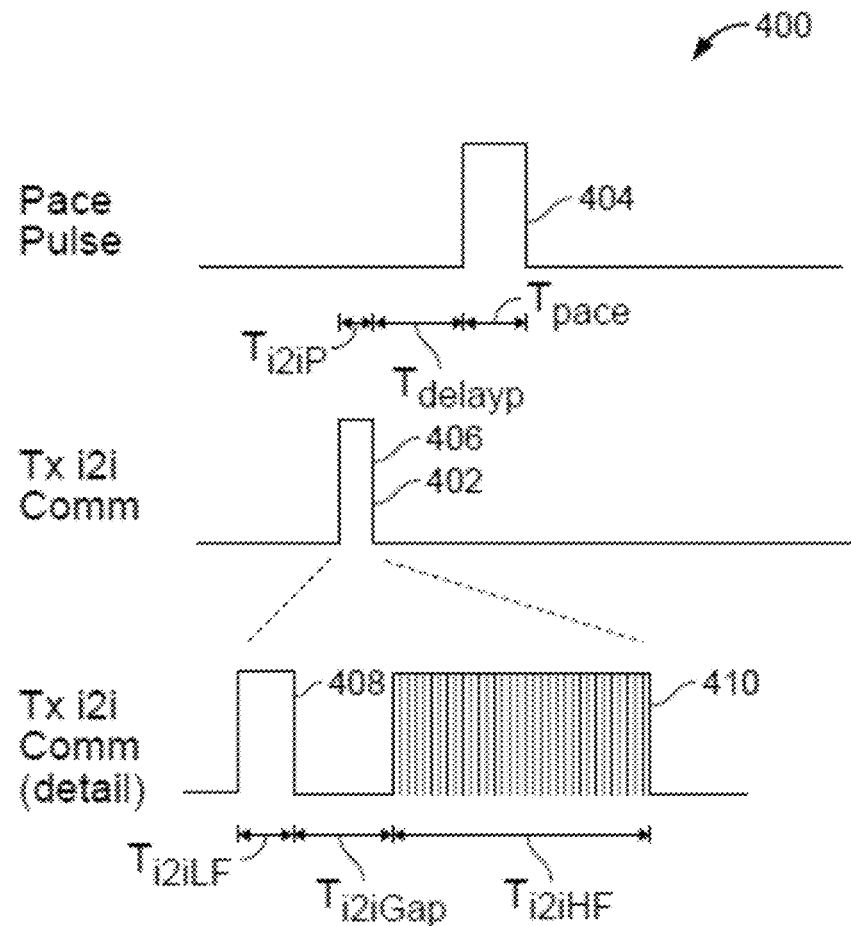
FIG. 4 is a timing diagram demonstrating one example of an implant-to-implant (i2i) communication for a paced event

FIG. 4 is a timing diagram 400 demonstrating one example of an i2i communication for a paced event. The i2i communication may be transmitted, for example, from LP 102a to LP 102b. As shown in FIG. 4, in this embodiment, an i2i transmission 402 is sent prior to delivery of a pace pulse 404 by the transmitting LP (e.g., LP 102). This enables the receiving LP (e.g., LP 102b) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 5:
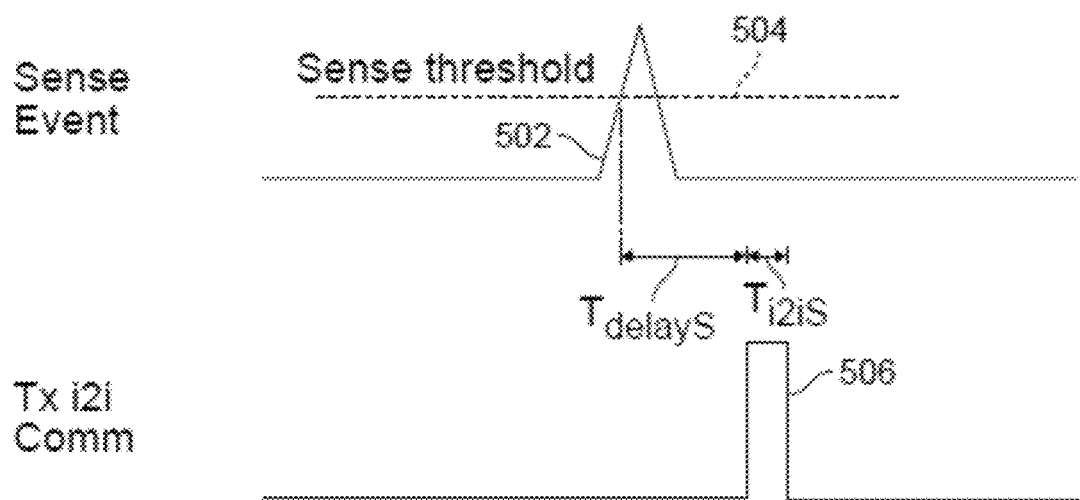
FIG. 5 is a timing diagram demonstrating one example of an i2i communication for a sensed event.

FIG. 5 is a timing diagram 500 demonstrating one example of an i2i communication for a sensed event. The i2i communication may be transmitted, for example, from LP 102a to LP 102b. As shown in FIG. 5, in this embodiment, the transmitting LP (e.g., LP 102a) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents example event markers sent from the aLP to the vLP, while Table 2 represents example event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a WI mode as the vLP does not depend on i2i communication to perform ventricular pace/sense activities. Once i2i communication is restored, the system 100 can automatically resume dual-chamber functionalities.

Messages that are transmitted between LPs (e.g., the aLP and the vLP) can be referred to herein generally as i2i messages, since they are implant-to-implant messages. As noted above, such messages can include event markers that enable one LP to inform the other LP of a paced event or a sensed event. For example, in certain embodiments, whenever the aLP senses an atrial event or paces the right atrium, the aLP will transmit an i2i message to the vLP to inform the vLP of the sensed or paced event in the atrium. In response to receiving such an i2i message, the vLP may start one or more timers that enable the vLP to sense or pace in the right ventricle. Similarly, the vLP may transmit an i2i message to the aLP whenever the vLP senses a ventricular event or paces the right ventricle.

The i2i messages that are sent between LPs may be relatively short messages that simply allow a first LP to inform a second LP of an event that was sensed by the first LP or caused (paced) by the first LP, and vice versa. Such i2i messages can be referred to herein as event marker i2i messages, or more succinctly as event i2i messages. The i2i messages that are sent between LPs, in certain instances, can be extended i2i messages that include (in addition to an event marker) an extension. In certain embodiments, an extended i2i message includes an event marker (e.g., 9 bits), followed by an extension indicator (e.g., 2 bits), followed by an extended message payload portion (e.g., 17 bits), followed by a cyclic redundancy check (CRC) code (e.g., 6 bits) or some other type of error detection and correction code.

In certain embodiments, whenever an i2i message is sent by an LP (or other type of IMD, such as a S-ICD), the i2i message will include an extension indicator so that the receiving LP knows whether or not the i2i message it receives includes an extension portion. In such embodiments, even a relatively short event i2i message will include an extension indicator. The extension indicator (e.g., 2 bits) is used by the LP (or other IMD) sending the i2i message to indicate, to the LP receiving the i2i message, whether or not the i2i message is an extended i2i message. In certain embodiments, if the LP receiving an i2i message determines based on the extension indicator bits that the received i2i message is not an extended i2i message, then the LP receiving the i2i message can ignore any bits that follow the extension bits. In such a case, the LP receiving the i2i message only decodes the event marker. On the other hand, if the LP receiving an i2i message determines based on the extension indicator bits that the received i2i message is an extended i2i message, then the LP receiving the i2i message will also decode the bits that follow the extension bits, and determine based on a CRC code (or other type of error detection and correction code), whether the i2i message is a valid message. If the extended i2i message is a valid i2i message, then the LP receiving the extended i2i message will as appropriate modify its operation, update parameters, and/or the like, based on information included in the extended i2i message. In certain embodiments, event i2i messages that are not extended i2i messages do not include any error detection and correction code.

In an extended i2i message, the event marker bits and the extension indicator bits are located, respectively, in an event marker field and an extension indicator field of an i2i message packet. In certain embodiments, the extended portion (that follows the event marker bits and the extension indicator bits) includes message bits (in a message field) and rate indicator bits (in a rate indicator field), which are parts of the payload. The payload can alternatively, or additionally, include other types of fields, such as an acknowledgement field that is used in certain situations for one LP to acknowledge reception of an i2i message from another LP of certain (e.g., critical) types of message.

More generally, various different types of information may be included within the payload of an extended i2i message. For one example, the payload can include a pacing rate indicator that enables one LP to inform another LP of a pacing rate. For example, assume that an LP system provides rate responsive pacing, wherein a pacing rate is adjusted in dependence on a patient's physical activity as detected, e.g., using an accelerometer, temperature sensor, and/or other type of sensor of an LP. In such an LP system, the vLP may inform the aLP of the rate at which the patient's heart should be paced so that the aLP and vLP can perform synchronized pacing. To achieve this, the vLP can send a pacing rate indicator to the aLP in the payload of an extended i2i message. The pacing rate indicator can, e.g., be a value indicating a pacing rate value (e.g., 80 bpm), a code that the aLP can look up (e.g., in a stored look up table) and corresponds to a pacing rate value, or a value that the aLP feeds into an equation to determine the pacing rate, but is not limited thereto. Alternatively, the pacing rate indicator can be beat-to-beat interval value (e.g., 0.75 seconds), a code that the aLP can look up and corresponds to a beat-to-beat interval value, or a value that the aLP feeds into an equation to determine the beat-to-beat interval, but is not limited thereto. Other variations are also possible and within the scope of the embodiments described herein.

Conductive Communication between an LP and External Programmer

Figure 6A:
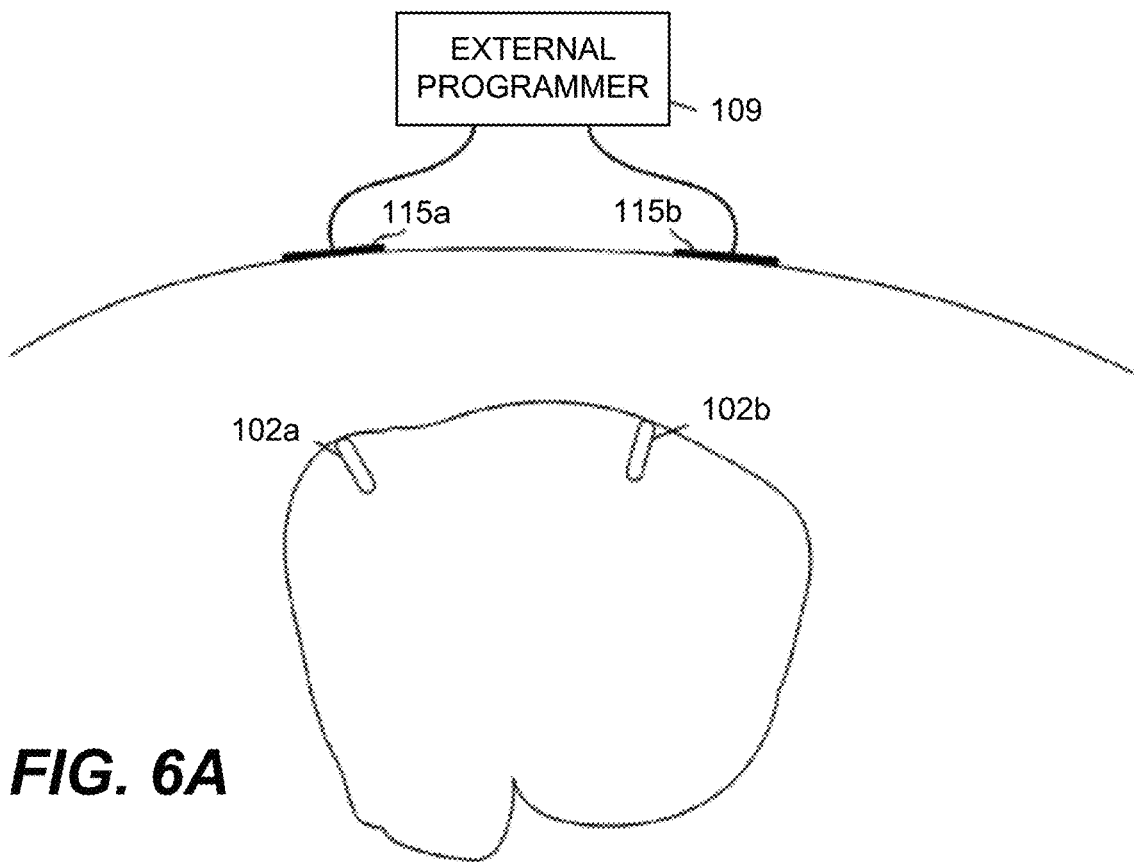
FIG. 6A depicts a sample configuration involving an external programmer and two endocardially implanted LPs.
Figure 6B:
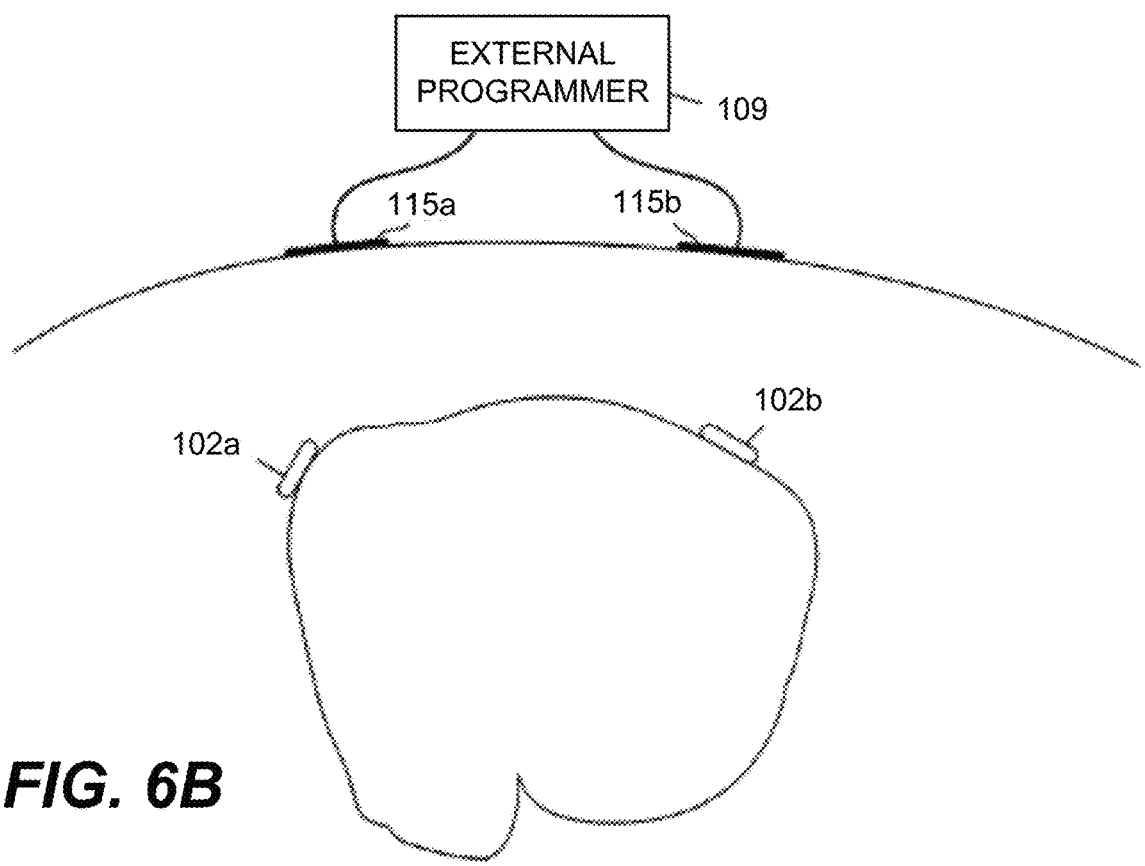
FIG. 6B depicts a sample configuration involving an external programmer and two LPs implanted epicardially (on the external heart surface).

FIGS. 6A and 6B are schematic pictorial views depicting how an external programmer can communicate with the LP 102a and/or the LP 102b via conductive communication, which is also referred to interchangeably herein as conducted communication. Such communication may take place via bidirectional communication pathways comprising a receiving pathway that decodes information encoded on pulses generated by one or more of the implantable devices 102a or 102b and conductive through body tissue to the external programmer 109. According to the illustrative arrangement, the bidirectional communication pathways can be configured for communication with multiple LPs 102a and 102b via two or more electrodes 108a and 108b and conduction through body tissue.

In accordance with certain embodiments, the external programmer 109 is connected by a communication transmission channel and has transmitting and receiving functional elements for a bidirectional exchange of information with one or more IMDs, such as LP 102a and/or LP 102b. The communication channel includes two or more programmer skin electrodes which can be affixed or secured to the surface of the skin. From the point of the skin, the communication transmission channel is wireless, includes the ion medium of the intra- and extra-cellular body liquids, and enables electrolytic-galvanic coupling between the programmer skin electrodes, which can also be referred to as surface electrodes, and the LPs, or more generally, IMDs. The bidirectional communication pathways can further comprise a transmitting pathway that passes information from the external programmer 109 to one or more of the LPs 102a and/or 102b by direct conduction through the body tissue by modulation that avoids skeletal muscle stimulation using modulated signals at a frequency in a range from approximately 10 kHz to 100 kHz, or at higher frequencies. For example, p2i communication signals may be transmitted at a center frequency (fc) of 500 kHz.

Information transmitted from the external programmer 109 to the implanted LPs is conveyed by modulated signals at the approximate range of 10 kHz to 100 kHz which is a medium-high frequency, or at higher frequencies. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. No restriction is imposed regarding location of electrode placement on the body because low signal attenuation enables the signal to travel throughout the body and to be received by the LPs 102a and 102b.

In some embodiments, the bidirectional communication pathways can further comprise a receiving pathway including a low-pass filter adapted to separate an electrocardiogram (ECG) from the information signals. The same surface electrodes 115 (also referred to as programmer skin electrode 115) that are used to transmit the information through the communication channel may also be used to detect a patient's electrocardiogram. Electrocardiogram frequencies are generally between 1 and 100 Hz, far lower than the 10 kHz to 100 kHz or higher range of frequencies used to transmit information through the communication transmission channel. Therefore, the electrocardiogram can be separated from the information signal by a low-pass filter and can optionally be displayed by the external programmer 109. In addition to low-pass filtering, blanking techniques that are typical in processing of cardiac signals can be used when the communication channel is active to prevent noise or erroneous signals from the communication channel affecting the electrocardiogram channel.

Because a plurality of LPs and/or other IMDs can be present, communication of information from the programmer may be detected by all devices, enabling information to be sent to each implanted device without sending the same information multiple times.

In various embodiments and applications, the bidirectional communication pathways can further comprise a transmitting pathway that passes information from the programmer 109 to the one or more LPs and/or other IMDs in a common communication event whereby information is sent to one or more target devices of the IMDs using a selected technique. For example, information specific to a single IMD or a subset of IMDs having a unique address can be assigned to the single IMD or the subset of IMDs and encoded in the information. In another technique, information can designate a specific function that is executed by a particular IMD or a particular subset of IMDs. The information is passed to one or more IMDs without sending individual address information for activating execution by the particular IMD or the particular subset of IMDs alone. In another technique, information can designate a specific function that is executed by a particular IMD or a particular subset of IMDs that have programming specific to the function adapted to recognize the received information is relevant to the function.

Specifically, information that is specific to a single IMD or a subset of IMDs can be sent. A unique address can be assigned to each IMD or subset. The address can be encoded in the information sent to the plurality of IMDs, and any individual IMD can make use only of information that matches either the address or the address of the subset to which the particular IMD belongs.

In another technique, if each IMDs or subset of IMDs serves a specific function, which is different from other IMDs, then information may be passed to the specific IMD or subset without the additional overhead of a group or individual address.

In some embodiments, the one or more IMDs can comprise one or more LPs that generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the electrodes for antenna-less and telemetry coil-less communication. For information transmitted from the LPs 102a and/and 102b to the external programmer 109, a communication scheme can be used in which the information is encoded on one or more pacing pulses. The pulse morphology is altered to contain the encoded information without altering the therapeutic benefits of the pacing pulse. The energy delivered by the pacing pulse remains essentially the same after the information is encoded. The external programmer 109 receives the pacing pulses through the associated surface electrodes 115. Encoded information is drawn from the pacing pulses and can contain state information of the implantable LP, such as battery voltage, lead impedance, sensed electrocardiogram amplitude, pacemaker current drain, programmed parameters, or other parameters.

The LPs 102a and/or 102b can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of an LP. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the LP. A gated segment is set sufficiently long in duration to enable accurate detection by the programmer 109, limiting the amount of information that can be transmitted during a single pacing pulse. Accordingly, a technique for communication can comprise generating stimulation pulses on stimulating electrodes of an IMD and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information.

The example described methods of encoding information on pacing pulses can use the external programmer 109 to distinguish pacing pulses from the patient's normal electrocardiogram, for example by recognition of the specific morphology of the pacing pulse compared to the R-wave generated during the cardiac cycle. For example, the external programmer 109 can be adapted to distinguish a generated cardiac pacing pulse from a natural cardiac depolarization in an electrocardiogram by performing comparative pattern recognition of a pacing pulse and an R-wave produced during a cardiac cycle.

The illustrative external programmer 109 and associated operating methods or techniques enable presentation to a user of information gathered from the LP(s) 102a and/or 102b and or other IMD(s) using conductive communication. Some of the information to be presented may include battery voltage, lead impedance, electrocardiogram amplitude, or current drain of the device. The information can be presented in addition to other information such as parameters to be set and programmed into the LP. The information can be presented to a user on a display screen. Some embodiments or configurations of an external programmer 109 can include a secondary link, for example either wireless or through a cable, to another display device, such as a handheld computer or terminal. The secondary link can also include communication over a local area network or the internet for display at a remote terminal.

FIG. 6A depicts a sample configuration involving the external programmer 109 and two endocardially implanted LPs 102a and 102b. The external programmer 109 is physically connected to the skin surface via two programmer skin electrodes 115a and 115b (also referred to as surface electrodes), which can serve three functions. The programmer skin electrodes 115a and 115b can be referred to individually as a programmer skin electrode 115 (or a surface electrode 115), or collectively as programmer skin electrodes 115 (or surface electrodes 115). First, the electrodes 115 can be used transmit encoded information from the programmer 109 to the LPs or other IMD(s) using a modulated signal, e.g., at a medium frequency 10 kHz to 100 kHz. Second, the programmer skin electrodes 115 can be used to receive information from individual LPs or other IMD(s) by detecting encoded information in the pacing pulses of the LP(s). Third, the programmer skin electrodes 115 can receive or sense a surface electrocardiogram for display and analysis by the programmer 109.

In FIG. 6A, the two LPs 102a and 102b are implanted endocardially. Alternatively, as shown in FIG. 6B, the two LPs 102a and 102b can be implanted by affixing to the exterior surface of the heart. The programmer skin electrodes 115 and the external programmer 109 function similarly in arrangements shown in FIGS. 4A and 4B whether the LPs 102a and 102b are implanted endocardially or epicardially (on the external heart surface). No restriction is imposed that the LPs are all implanted inside or all implanted outside the heart. One or more may be implanted endocardially along with others implanted on the outer surface of the heart. The functioning of the programmer 109 is substantially the same. Although two programmer skin electrodes 115 are shown in FIGS. 6A and 6B, two is generally the minimum number of programmer skin electrodes required for adequate conductive communication. More programmer skin electrodes 115 can be used, enabling an ECG to be sensed at multiple vectors for better analysis. More than two programmer skin electrodes may also enable a choice of vectors for conductive communication with the LPs, thereby maximizing the signal to noise ratio of the system. FIGS. 6A and 6B each depict two LPs 102a and 102b. One, two, or more LPs can be implanted, depending on the number of pacemakers appropriate for effective therapy.

In various embodiments, the external programmer 109 can be configured to perform one or more operations such as electrocardiogram sensing, retrieving status information from implanted pacemakers, modifying configuration parameters of multiple implanted pacemakers simultaneously in information passed through a common electrode set, displaying electrocardiograms, displaying information received from the at least one implantable device, and/or others.

In various embodiments, an LP can manage power consumption to draw limited power from an internal battery, thereby reducing device volume. Each circuit in the LP can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit can be throttled to recharge the tank capacitor at constant power from the battery. The one or more LPs can be configured to charge the tank capacitor in preparation for stimulation pulse generation, time one or more windows between pulse generation, disable charging of the tank capacitor during the one or more timed windows, and enable a receive amplifier in the implanted biostimulator while the tank capacitor is disabled.

In some embodiments, the external programmer 109 can detect a stimulation pulse from an LP and transmit data after a selected delay to coincide with a window that the LP's receiving amplifier is enabled.

The LP(s) and/or other IMD(s) can encode and/or decode information using various techniques such as encoding the information using pacing pulse width, binary-coded notches in a pacing pulse, modulation of off-time between pacing pulses, or other suitable encoding techniques. The external programmer 109 can encode and/or decode information using on-off keying encoding and modulation techniques. However, any other appropriate method can be used whereby a modulated bit-stream can be generated at a medium high frequency, for example frequency-shift keying, frequency modulation, or amplitude shift keying.

External Device (Non-Programmer) for Remote Follow-Up Communication with LP(s)

In order for an LP to be interrogated by or otherwise communicate with an external programmer (e.g., 109), a patient (within which the LP is implanted) needs to visit a medical facility that has an external programmer, as mentioned above. This is time consuming for both the patient and the medical personnel, as well as costly to the patient in terms of increasing their medical bills. It would be beneficial if an LP can be interrogated from time to time without requiring the use of an external programmer and without requiring that a patient visit a medical facility.

Certain embodiments of the present technology are related to external devices (aka remote monitors) that are capable of receiving and deciphering conductive communication signals from one or more implanted LPs. Such an external device includes or is communicatively coupled to at least two electrodes for use in receiving conductive communication signals from one or more LPs implanted in a patient. In specific embodiments, the external device includes three electrodes. Such electrodes can be used to sense a 1 lead or 3 lead ECG, or even a 6 lead ECG, which ECGs can be displayed on a display of the external device. Alternatively, or additionally, ECG data can be stored within a memory of the external device and/or transmitted to a patient care network for storage, viewing and/or analysis. In certain embodiments, the external devices wirelessly connects to a smartphone, tablet computer, or other portable computing device using Bluetooth, or WiFi, or some other type of RF communication technology. In certain designs, the smartphone or other type of portable computing device can utilize WiFi and/or direct cellular communication or wireless broadband to provide notification information and/or other types of diagnostic information obtained from an implanted LP to a patient care network. Information received from an LP can include model and/or serial numbers, device settings, new stored information since the last follow-up session and/or battery status, etc. Stored electrogram data can also be included. The external device (aka remote monitor) is preferably small, portable, and lightweight so it travels well. Additionally, the external device is preferably easy for a patient to handle, making electrode-skin contact straight forward.

Figure 7A:
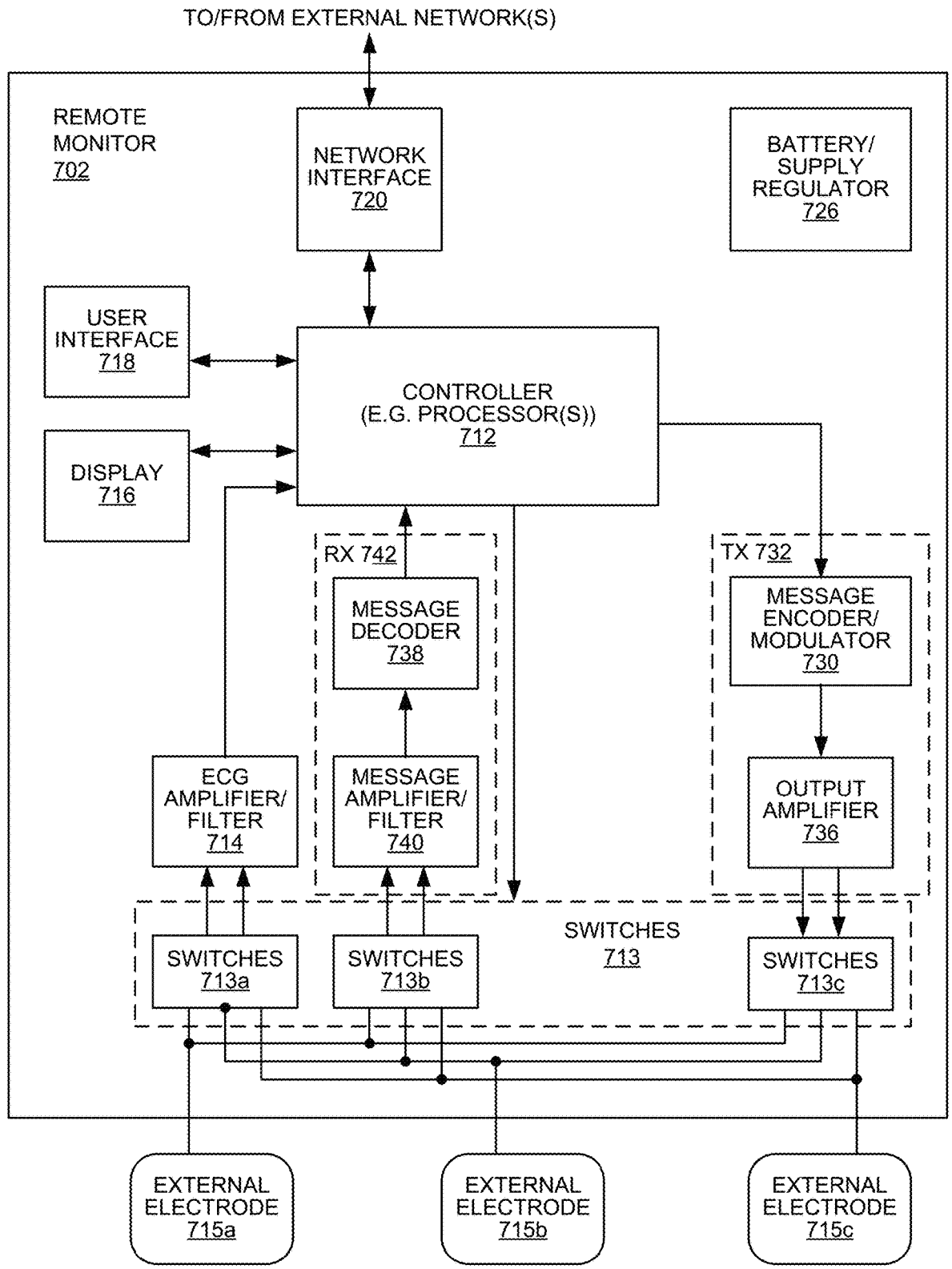
FIGS. 7A and 7B are block diagrams illustrating example details of a remote monitor in accordance with certain embodiments of the present technology.
Figure 7B:
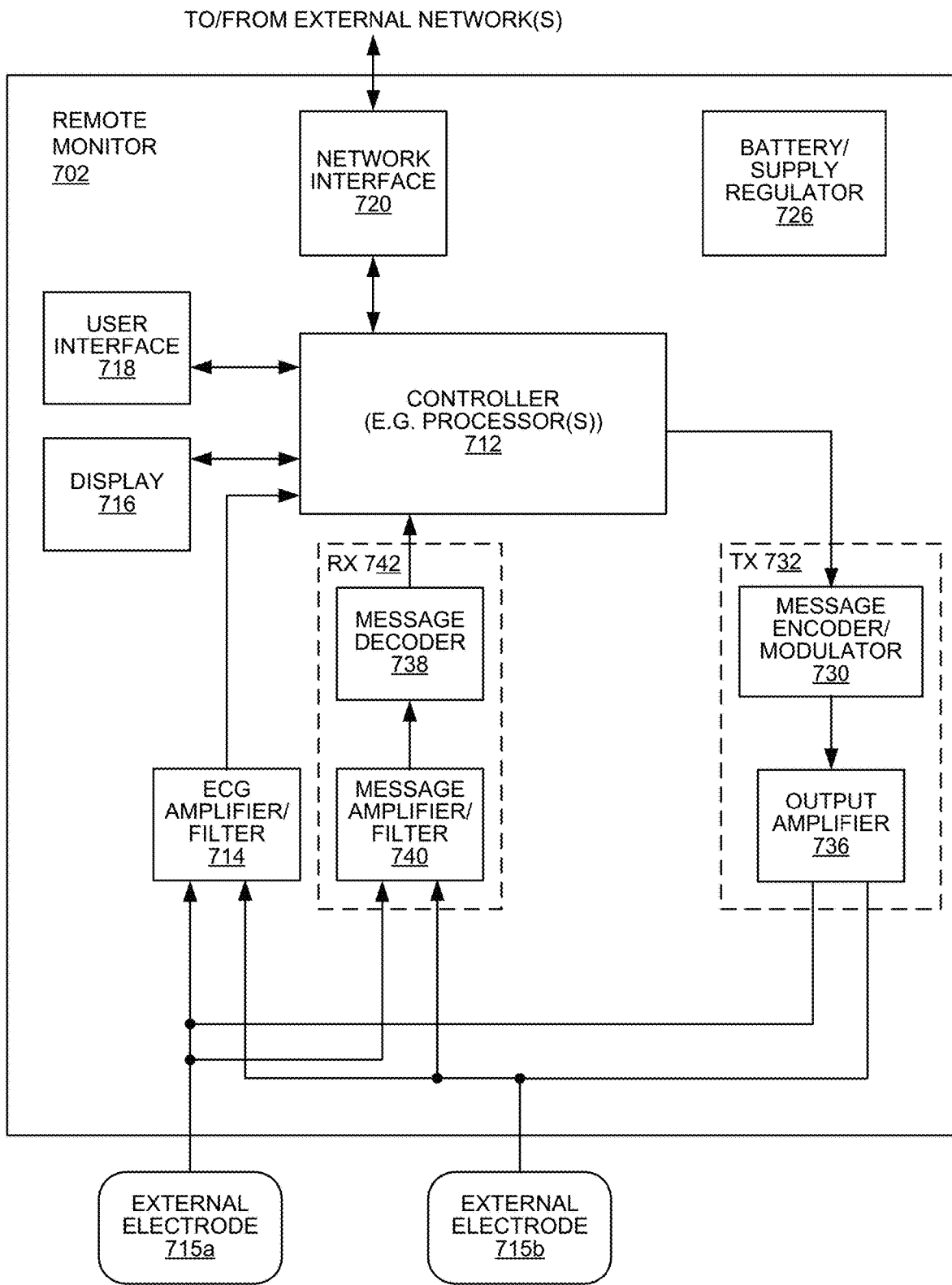

FIG. 7A is a block diagram illustrating example details of a remote monitor 702 in accordance with some implementations, wherein the remote monitor 702 can also be referred to as an external device 702. The external device 702 that can be used to receive diagnostic information from an LP (e.g., 102a and/or 102b) from time to time without requiring the use of an external programmer (e.g., 109). In contrast to an external programmer (e.g., 109), the external device 702 (aka remote monitor) is incapable programming an LP or otherwise directly altering any therapy functionality of the LP from which external device 702 obtains information. Accordingly, if the external device 702 obtains information from an LP that indicates that certain modifications should be made to the LP, the external device 702 can either provide a patient notification that informs the patient they should visit a medical facility, and/or the external device can transmit a notification and/or other information to a patient care network. Accordingly, it should be appreciated that the external device 702 may be less sophisticated than a typical external programmer, or can be implemented (at least partially) using a smart phone or the like, to enable such an external device to be more affordable and more readily available to patients to provide for remote follow-up capabilities. Thus, it should be appreciated that patients that own or otherwise have access to the external device 702 may not be required to visit a medical facility as often as they would otherwise need to if they did not own or otherwise have access to the external device 702.

As will be explained in additional details below, in certain embodiments the remote monitor 702 does not output any pulses or other signals that are detectable by an LP implanted within the patient, and thus, the LP is unaware of whether any instances of the sequence of pulses that the LP outputs are received by the external device 702. In other embodiments, the remote monitor 702 can send an acknowledgement sequence of pulses, which informs an LP that the remote monitor 702 is in proximity to the LP and capable of receiving data (encoded into conducted communicate pulses) from the LP. However, regardless of the embodiment, the remote monitor 702 is not capable of programming or otherwise modifying the therapeutic operation of the LP. This is one way that the remote monitor 702 differs from the external programmer 109. The remote monitor 702 can also be referred to herein as an external remote monitor 702, as an external remote monitor device 702, or more succinctly as an external device 702. The term external, as used in these phrases, means the monitor/device is not implanted within a patient, and is not configured for implantation.

Referring to FIG. 7A, a schematic block diagram shows an embodiment of the remote monitor 702 adapted for receiving conductive communication signals from one or more LP(s) (e.g., 102a and/or 102b), in order to perform remote monitoring of the LP(s). The remote monitor 702 is shown as including a controller 712, a display 716, a user interface 718, a network interface 720, and a battery/supply regulator 726. The battery and/or supply regulator 726 provides one or more constant voltages to the various components of the remote monitor 702 during normal operation. The remote monitor 702 is also shown as including an ECG amplifier and/or filter 714, a conductive communication receiver (RX) 742, and an optional conductive communication transmitter (TX) 732. The receiver 742, in this example embodiment, is shown as including a message amplifier and/or filter 740, and a message decoder 738, and is configured to receive conductive communication signals from one or more LPs (e.g., 102a and/or 102b). The controller 712, which is used to control the operation of the remote monitor 702, can include, e.g., one or more processors (or equivalent control circuitry), RAM and/or ROM memory, logic and timing circuitry, state machine circuitry, and/or I/O circuitry, but is not limited thereto. The controller 712 can also include a clock circuit, or a separate clock circuit (not shown) can provide a clock signal to the controller 712.

In the embodiment shown in FIG. 7A, the remote monitor 702 is shown as being connected to three external electrodes 715a, 715b, and 715c, which can be referred to collectively as the electrodes 715, or individually as an electrode 715. The electrodes 715 are shown as being connected to switches 713, which are shown as including first, second, and third sets of switches 713a, 713b, and 713c. The external electrodes 715 can be located on a housing of the remote monitor 702, or can be separate from such a housing. Where the electrodes 715 are separate from a housing of the remote monitor 702, the electrodes 715 can be attached to a further housing that is communicatively coupled to the remote monitor 702 via one or more wires, or via a wireless connection, e.g., using Bluetooth or WiFi, but not limited thereto. The electrodes 715, as will be described in more detail below, can be used to receive conductive communication signals from one or more LPs, and optionally can also be used to sense an electrocardiogram (ECG).

The electrodes 715 are intended to come into contact with the skin of a patient. For example, the electrodes 715 can be configured to be touched by one or more digits on each hand of a patient, or to come into contact with a patient's wrist or a patient's chest, but are not limited thereto. Example formfactors of the remote monitor 702, and its electrodes 715, are discussed below with reference to FIGS. 8A-8C. A set of switches 713a is connected between the electrodes 715 and the ECG amplifier and/or filter 714, a set of switches 714b is connected between the electrodes 715 and the receiver 742, and a further set of switches 713c is connected between the electrodes 715 and the transmitter 732. The various sets of switches are controlled by the controller 712. In certain embodiments, the amplifiers and/or filters 714, 740, and 736 are each differential circuits that are intended to be connected to a pair of the electrodes 715 by the switches 713 under the control of the controller 712. For an example, the switches 713b can be controlled to connect any pair of the electrodes 715a, 715b, 715c to the message amplifier and/or filter 740. For an example, the switches 713*b* can connected the electrode 715*a* to a first input of the message amplifier/filter 740, and connect the electrode 715*b* to a second input of the message amplifier/filter 740, and not connect electrode 715*c* to any input of the message amplifier/filter 740. It is also possible that the switches can connect two electrodes 715 directly to one another to effectively form a larger electrode. For an example, the switches 713*b* can connect the electrode 715*a* to a first input of the message amplifier/filter 740, and connect the electrodes 715*b* and 715*c* to one another and to a second input of the message amplifier/filter 740. The inclusion of three electrodes 715 enables an ECG to be sensed at multiple vectors and/or enables selection from among the multiple vectors for conductive communication with one or more implanted LPs so that system signal-to-noise ratio can be improved or maximized.

As noted above, the conductive communication receiver 742, which is shown as including the message amplifier and/or filter 740, and the message decoder 738, is configured to receive conductive communication signals from one or more LPs (e.g., 102*a* and/or 102*b*). The message amplifier and/or filter 740 is configured to amplify and/or filter conductive communication signals received from an LP (e.g., 102*a* and/or 102*b*). The amplifier portion can be used to increase the relatively small amplitudes of such conductive communication signals. The filter portion can be a high-pass filter or a bandpass filter adapted to separate an ECG signal from conductive communication signals. The message decoder 738 can be configured to decode conductive communication signals received from an LP into a format that the controller 712 can understand. The specific type of decoding performed by the message decoder 738 depends upon the specific coding of the conductive communication signals received from an LP, e.g., on-off keying, frequency-shift keying, frequency modulation, or amplitude shift keying, but not limited thereto.

The optional conductive communication transmitter 732, if present, is configured to send (under the controller of the controller 714) a remote monitor acknowledgement (ACK) sequence of conductive communication pulses, which informs one or more LPs that the remote monitor 702 is in proximity to the LP(s) and capable of receiving data (encoded into conducted communicate pulses) from the LP(s). The remote monitor ACK may be used, e.g., where the "active" remote follow-up method for enabling an LP (e.g., 102*a* and/or 102*b*) to provide diagnostic information to an external device (aka remote monitor, e.g., 702) is implemented, as described below with reference to FIGS. 10A and 10B, which can be collectively referred to as FIG. 10. The remote monitor ACK may also be used, e.g., with certain "hybrid" remote follow-up techniques described below.

The transmitter 732, in this example embodiment, is shown as including a message encoder and/or modulator 730 and an amplifier 736. The message encoder and/or modulator 730 can be configured to encode and/or modulate signals that are output from the controller 712 into a format that LP(s) can understand. The specific type of encoding performed by the message encoder depends upon the specific type of encoding the LPs can understand, e.g., on-off keying, frequency-shift keying, frequency modulation, or amplitude shift keying, but not limited thereto. The amplifier 736 is coupled to the encoder/modulator 732 to increase amplitudes of pulses included in an ACK sequence to a level sufficient to enable an LP to receive acknowledgements from the remote monitor 702.

The controller 712 receives ECG data and optionally displays an ECG using the display 716 and can also display information included in other data acquired from the implanted LP(s) acquired through the encoded pulses included in conductive communication signals, such as battery voltage, lead impedance, sensed cardiac signal amplitude, or other system status information. The controller 712 also can accept input from a user via a user interface 718, which can include, e.g., a keyboard and/or touchscreen, but is not limited thereto. The controller 712 can also communicate over a network interface 720 to other data entry or display units, such as a handheld computer or laptop/desktop unit. The network interface 720 can be cabled or wireless and can also enable communication to a local area network or the Internet for greater connectivity. More specifically, the network interface 720 can be used to send ECG data, diagnostic data, and other types of data collected from one or more LPs to a patient care network associated with a medical group and/or facility. For more specific examples, the network interface can include a Bluetooth antenna, a WiFi antenna, and/or an Ethernet connection, but is not limited thereto.

The controller 712, which can include one or more processors, and/or the like, can execute operations based on firmware stored in non-volatile memory (Flash). The non-volatile memory can also be used to store parameters or values that are to be maintained when power is removed. The controller 712 can use volatile memory or random access memory (RAM) as general storage for information such as ECG data, status information, swap memory, and other data.

The remote monitor 702 can include or be coupled to more or less than three external electrodes 714. For example, in the embodiment shown in FIG. 7B, the remote monitor 702 includes or is coupled to only two external electrodes 715, thereby eliminating the need for the switches 713.

The external electrodes (e.g., 715) of a remote monitor (e.g., 702) described herein can be used to sense ECG signals, as well as sense conductive communication signals output by one or more implanted LPs. It is also possible for the external electrodes of a remote monitor to be used to receive electrogram (EGM) signal data included in conductive communication signals output by one or more LPs, which EGM signal data can be received by the remote monitor (using the external electrodes) and used to reproduce one or more electrogram (EGM) signals that were sensed by one or more LPs, wherein an EGM signal can also be referred to as an intracardiac electrogram (IEGM) signal. Instead of, or in addition to, being able to communicate with one or more IMDs via conductive communication, the remote monitor 702 can have an antenna and RF communication capabilities that enable the remote monitor 702 to wirelessly communicate with an implantable device, such as the ICM 104, via a wireless communication protocol, examples of which were discussed above.

The remote monitor 702, which can also be referred to as an external device, can take many physical forms, but fundamentally it should be able to establish a conductive vector with the patient so that it can detect the LP's conductively communicated transmissions, decipher the communication protocol utilized by the LP, and upload any acquired follow-up information to a patient care network, such as the Merlin.Net™ patient care network operated by Abbott Laboratories (headquartered in the Abbott Park Business Center in Lake Bluff, Ill.). In certain embodiments that utilize a specific remote follow-up protocol, the external device should also be able to transmit an appropriate code (e.g., an ACK code) to the target LP per an established protocol. In this latter case, to maintain strong cybersecurity, the external device may be designed such that its hardware is capable of generating and transmitting only that singular 'appropriate code' (i.e., not software-configurable).

Figure 8A:
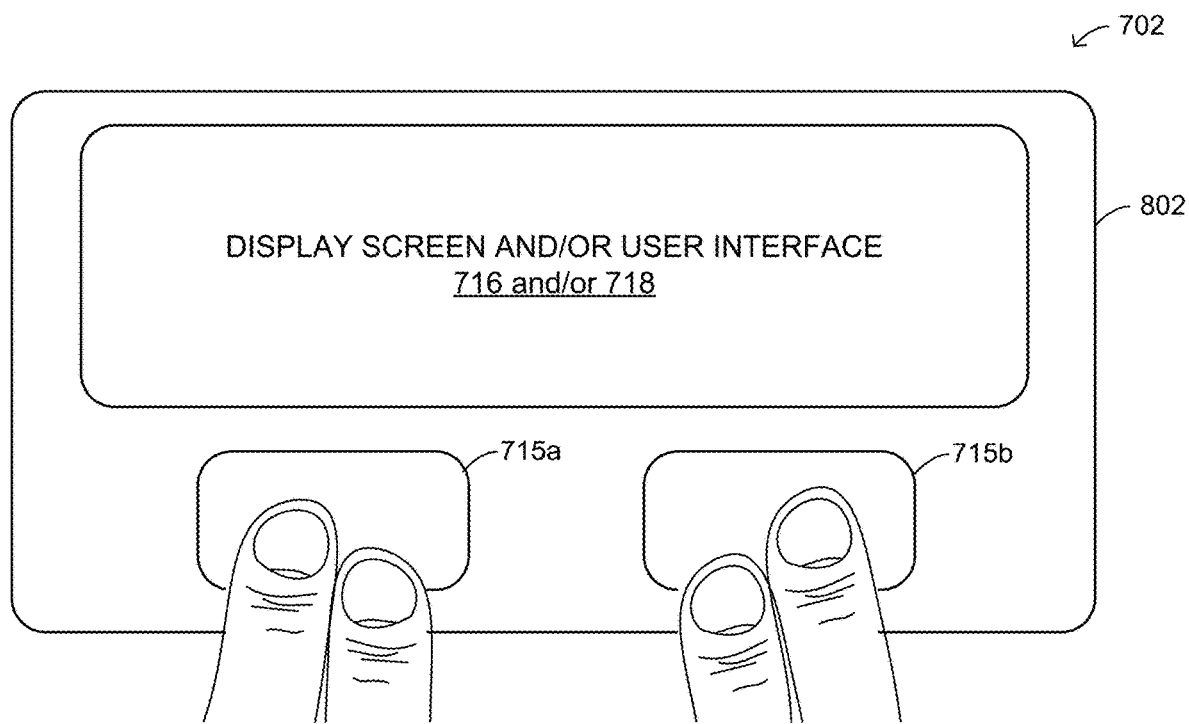
FIGS. 8A-8C illustrates various different formfactors of the remote monitor according to various different embodiments of the present technology.

FIG. 8A illustrates an example physical formfactor of the remote monitor 702. In FIG. 8A, the remote monitor 702 includes a housing 802 that houses all of the components of the remote monitor 702, including the electrodes 715. Only two electrodes 715 (i.e., 715a and 715b) are shown in FIG. 8A. However, a third electrode (e.g., 715c) can be located on a backside of the housing 802.

Figure 8B:
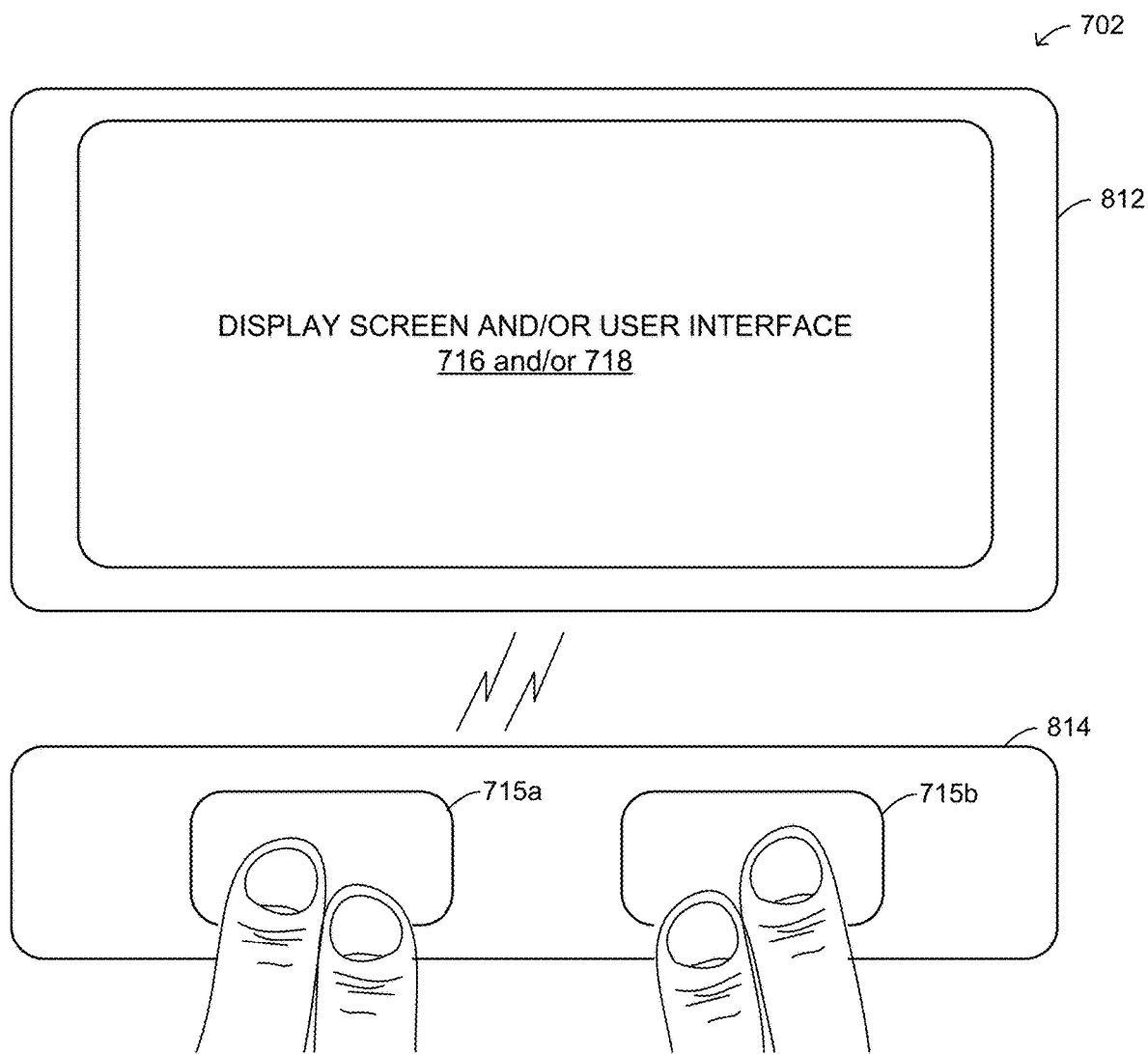

FIG. 8B illustrates another example formfactor of the remote monitor 702. In FIG. 8B, the remote monitor 702 includes a housing 812 that houses all of the components of the remote monitor 702, except for the electrodes 715. In this embodiment the electrodes are included in a separate housing 814 that is communicatively coupled to the remote monitor 702 via one or more wires, or via a wireless connection, e.g., using Bluetooth or WiFi, but not limited thereto. Only two electrodes 715 (i.e., 715a and 715b) are shown in FIG. 6B. However, a third electrode (e.g., 715c) can be located on a backside of the housing 814.

Figure 8C:
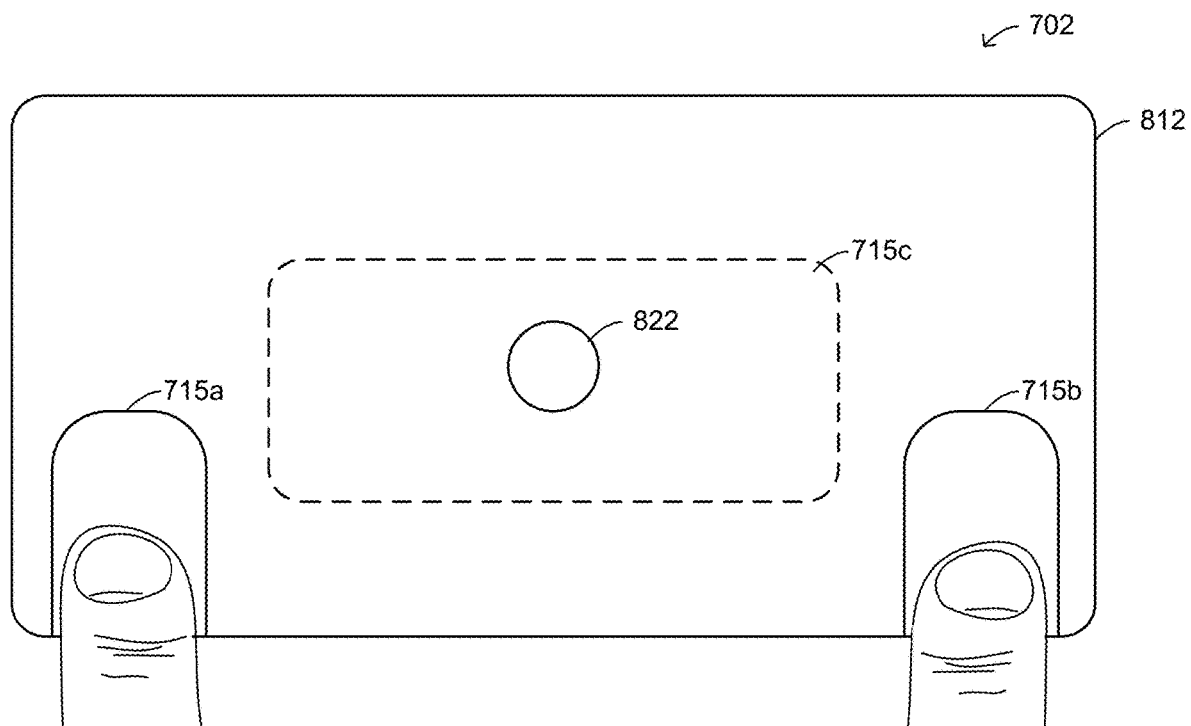

In still another embodiment, portions of a remote monitor, such as the display 716, user interface 718, network interface 720, and at least a portion of the controller 712, are implemented using a smartphone, tablet computer, or other type of off-the-shelf computing device, and further portions of the remote monitor, such as the electrodes 715, ECG amplifier and/or filter, the receiver 742, and the optional transmitter 732, are implemented by a custom device including a housing that houses such elements. An example of such an embodiment is shown in FIG. 8C. Referring to FIG. 8C, the remote monitor 702 is shown as including a housing 812 which includes a pair of electrodes 715a and 715b on the front of the housing 812, and a larger electrode 715c (shown in dashed line) on the backside of the housing 812. A patient can put their left thumb on the electrode 715a and their right thumb on the electrode 715a. In one embodiment, the electrode 715a also includes a portion thereof located on the backside of the housing 812, such that while the patient's left thumb is on the portion of the electrode 715a on the front of the housing, the patient can place their left forefinger on the portion of the electrode 715a that is on the backside of the housing. Similarly, the electrode 715b can also include a portion thereof located on the backside of the housing 812, such that while the patient's right thumb is on the portion of the electrode 715b on the front of the housing, the patient can place their right forefinger on the portion of the electrode 715b that is on the backside of the housing. The electrodes 715a and 715b can be flat metal (e.g., steel) plates on which thumbs and/or digits are placed, or hollowed out metal electrodes into which thumbs and/or other digits are placed. The electrode 715c on the backside of the housing 812 can be generally flat such that it can be rested on a patient's leg, e.g., on their upper thigh, calf or ankle. The electrode 715c can provides a third contact point to a patient's skin, which is especially useful if a strength of conductive communication signals received just using the electrodes 715a and 715b are deemed too weak or small. In an embodiment, the electrode 715c can be spilt substantially down the middle along the long axis of the rectangle to provide an electrode for detecting the signal while the other half may be designated as a ground.

On the front of the housing is located a magnet 822 (e.g., a thin cylindrical neodymium magnet) that is used to hold a smartphone in place, where a ferromagnetic plate has been adhered or otherwise been attached to a backside of the smartphone (not shown in FIG. 8C). The components of the remote monitor 702 shown in and discussed with reference to FIG. 7A, or just some of those components, can be included within the housing 812. The display 716, user interface 718, network interface 720, and at least a portion of the controller 712, in this embodiment are implemented using a smartphone that is magnetically or otherwise attached to the housing 812 in FIG. 8C. An application that is installed on such smartphone can provide the functionality used to perform the various embodiments described herein. Other components, such as the ECG amplifier and/or filter 714, the receiver 742, and the optional transmitter 732, can be included within the housing 812. Other variations are also possible and within the scope of the embodiments described herein.

Remote Follow-Up Capabilities for LPs

Various techniques for providing an LP (e.g., 102a and/or 102b) with remote follow-up capabilities are disclosed herein, which techniques enable the LP to provide diagnostic information to an external device (aka remote monitor, e.g., 702) that is incapable of programming the LP. The fact that the external device (aka remote monitor, e.g., 702) cannot program the LP is a major distinguishable feature between the external device (aka remote monitor) and an external programmer (e.g., 109). In each of these embodiments, the LP includes two or more implantable electrodes (e.g., 108a and 108b) used to output both pacing pulses and conductive communication pulses. Further, in certain embodiments the external device (aka remote monitor, e.g., 702) includes or is communicatively coupled to two or more external electrodes (e.g., 715) used to receive conductive communication pulses from the LP. Conductive communication signals, as the term is used herein, include conductive communication pulses. Instead of, or in addition to being able to communicate with IMDs via conductive communication, a remote monitor can have an antenna and RF communication capabilities that enables the remote monitor 702 to wirelessly communicate with an implantable device, such as the ICM 104, via a wireless communication protocol, examples of which were discussed above. In such embodiments, the ICM 104 may perform conductive communications with one or more LPs 102a and/or 102b, and the ICM 104 can act as a bridge communication device between the LPs 102a and/or 102b and an external programmer 109 and/or a remote monitor (e.g., 702 described below with reference to FIGS. 7A and 7B).

Passive Remote Follow-Up

Figures 9A, 9B:
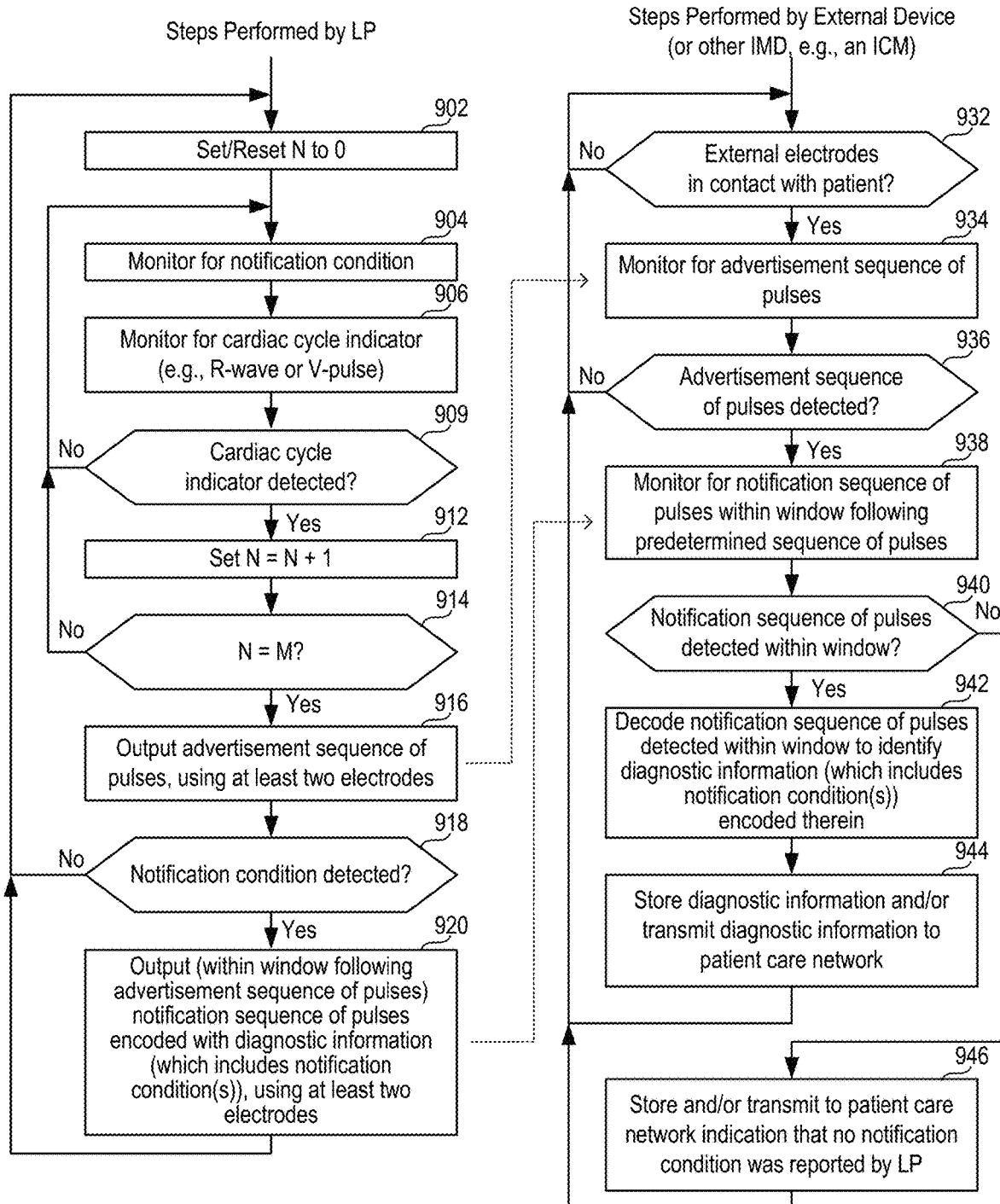
FIGS. 9A and 9B, which can be collectively referred to as FIG. 9, include a high level flow diagram that is used to summarize a "passive" remote follow-up method for enabling an LP to provide diagnostic information to an external device (aka remote monitor) in accordance with certain embodiments of the present technology.

FIGS. 9A and 9B, which can be collectively referred to as FIG. 9, include a high level flow diagram that is used to summarize a "passive" remote follow-up method for enabling an LP (e.g., 102a and/or 102b) to provide diagnostic information to an external device (aka remote monitor, e.g., 702). The steps shown in FIG. 9A are performed by an LP, e.g., 102a or 102b. The steps shown in FIG. 9B are performed by an external device (aka remote monitor, e.g., 702).

Initially referring to FIG. 9A, step 902 involves setting or resetting a cardiac cycle count value N to zero. Step 904 involves monitoring for one or more notification conditions. The notification condition(s) monitored for at step 904 can be associated with the LP. Examples of notification conditions that are associated with the LP include, but are not limited to, a recommended replacement time (RRT) condition, a device reset condition, an end of service (EOS) condition, a high current condition, a memory region full condition, a memory corruption condition, a poor conductive communication condition, and/or the like. Alternatively, or additionally, the notification condition(s) monitored for at step 904 can be associated with the patient within which the LP is implanted. Examples of notification conditions associated with the patient include, but are not limited to, an arrhythmia detection, a non-cardiac physiological condition detection, an increased pacing burden detection, an automatic mode switching (AMS) detection, a pacemaker mediated tachycardia (PMT) detection, a premature ventricular contraction (PVC) detection, and/or the like.

Step 906 involves monitoring for a cardiac cycle indicator. For example, where the LP (e.g., 102b) is implanted in the right ventricle, the LP can monitor for the detection of an R-wave or the detection or generation of a V-pulse. For another example, were the LP (e.g., 102a) is implanted in the right atrium, the LP can monitor for the detection of a P-wave or the detection or generation of an A-pulse. At step 909 there is a determination of whether a cardiac cycle indicator was detected, and if so (i.e., if the answer to the determination at step 909 is Yes), then the cardiac cycle count value N is incremented in step 912 using the equation set N=N+1. If the answer to the determination at step 909 is No, then flow returns to step 904 and steps 904, 906, and 909 are repeated until the answer to the determination at step 909 is Yes.

After the cardiac cycle count value N is incremented at step 912 there is a determination of whether the cardiac cycle count value N has reached a threshold value M, i.e., at step 914 there is a determination of whether N=M. For an example, the threshold value M can equal eight, but lower or higher threshold values can alternatively be used. If the answer to the determination at step 914 is No, then flow returns to step 904. If the answer to the determination at step 914 is Yes, then flow goes to step 916. At step 916 an advertisement sequence of pulses is output using at least two electrodes of the LP, irrespective of whether the LP recognizes the presence of at least one notification condition. In accordance with certain embodiments, the advertisement sequence of pulses is a predetermined sequence of pulses that indicates to an external device (aka remote monitor, e.g., 702) and/or an external programmer (e.g., 109) that an LP is implanted within a patient. The advertisement sequence of pulses can also be referred to as a sniff sequence of pulses, or more succinctly as a sniff. In an alternative embodiment, where N is decremented rather than incremented, at step 902 N is set or reset to be equal to M, at each instance of step 912 N is decremented using the equation N=N−1, and at each instance of step 914 there is a determination of whether N=0.

At step 918 there is a determination of whether a notification condition had been detected at an instance of step 904. If the answer to the determination at step 918 is No, then flow returns to step 904. If the answer to the determination at step 918 is Yes, then flow goes to step 920. At step 920, the LP outputs a notification sequence of pulses, using at least two of its electrodes, within a notification transmission window following the outputting of the advertisement sequence of pulses. The notification sequence of pulses (which is encoded with diagnostic information associated with the LP and/or associated with the patient within which the LP is implanted) that is output at step 920 can be referred to as a passive out-of-session (OOS) alert, since it is sent while the LP is not in a communication session with an external programmer (e.g., 109). The term "passive" indicates that the alert is sent without any acknowledgement or other feedback from an external device. The advertisement sequence of pulses (output at step 916) and the notification sequence of pulses (output at step 920) and/or information encoded therein are capable of being received by an external device (aka remote monitor, e.g., 702) that includes or is communicatively coupled to two or more external electrodes that are in contact with the patient's skin and used to receive conductive communication pulses from the LP.

Following step 920, flow returns to step 902, at which the cardiac cycle count value is reset to 0, by setting N=0. Steps 904 through 920 are then repeated. In summary, the steps summarized with reference to FIG. 9A result in the LP periodically outputting an advertisement sequence of pulses, using at least two of the two or more implantable electrodes of the LP, irrespective of whether the LP recognizes the presence of at least one notification condition. Where the threshold value M equals eight, then the method summarized with reference to FIG. 9A will results in the advertisement sequence being output once every eight cardiac cycles. Wherever there is a notification condition detected, the LP will also output a notification sequence of pulses, using at least two of the two or more implantable electrodes of the LP, within a notification transmission window following the outputting of the advertisement sequence of pulses. The steps summarized with reference to FIG. 9A occur whether or not there is an external device with electrodes in contact with the patient and listening for the advertisement sequence of pulses and possible notification sequence of pulses. Both the advertisement sequence of pulses and the notification sequence of pulses can be transmitted during a cardiac refractory period.

FIG. 9B will now be used to summarize steps that can be performed by an external device (aka remote monitor, e.g., 702), or by another IMD (e.g., an ICM). Referring to FIG. 9B, at step 932 there is a determination of whether external electrodes of the external device (or communicatively coupled to the external device) are in contact with the skin of a patient. If the answer to the determination at step 932 is No, then flow returns to step 932. If the answer to the determination at step 932 is Yes, then flow goes to step 934. Where an IMD (e.g., an ICM) is to perform the steps in FIG. 9B, step 932 can be skipped. At step 934 the external device (or other IMD) monitors for the predetermined sequence of pulses known as the advertisement sequence of pulses (which are periodically transmitted by the LP at instances of step 916 discussed above with reference to FIG. 9A). At step 936 there is a determination of whether the advertisement sequence of pulses was detected. If the answer to the determination at step 936 is No, the flow returns to step 932. If the answer to the determination at step 936 is Yes, the flow goes to step 938.

At step 938 the external device (or other IMD) monitors for a further sequence of pulses (i.e., a notification sequence) within a window following the advertisement sequence detected at a most recent instance of 936. At step 940 there is a determination of whether a notification sequence is detected within the window. If the answer to step 940 is No, then flow goes to step 946, at which step an indication that no notification condition was reported by the LP is stored within the memory of the external device and/or transmitted to a patient care network. In other words, if the external device (or other IMD) detects an advertisement sequence but does not detect a notification sequence within a specified window following the advertisement sequence, then the external device (or other IMD) is able to conclude that the LP had not detected and reported a notification condition, and thus, that everything is okay with the LP and/or patient, and can record and/or forward such information.

Returning to step 940, if the answer to the determination at step 940 is Yes, meaning a notification sequence was detected within the specified window following the detection of the advertising sequence, then flow goes to step 942. At step 942 the external device (or other IMD) decodes the notification sequence of pulsed detected within the window to identify diagnostic information, which includes one or more notification conditions encoded therein. At step 944 the external device (or other IMD) stores within its memory and/or transmits to a patient care network the diagnostic information it received from the LP. Following step 944 or 946 flow returns to step 932.

The remote follow-up method described with reference to FIGS. 9A and 9B, which can be collectively referred to as FIG. 9, can be referred to as the "passive" remote follow-up method because the LP has no knowledge of when an external device (aka remote monitor) is actually receiving the diagnostic information it includes in a notification sequence of pulses, and the external device (aka remote monitor) never tells the LP it is listening for a notification sequence of pulses. In other words, in the embodiment summarized with reference to FIG. 9, the external device (or other IMD) does not output any pulses or any other signals that are detectable by the LP implanted within the patient, and thus, the LP is unaware of whether any instances of the advertisement sequence of pulses and the notification sequence of pulses that the LP outputs are received by an external device (or other IMD). Further, since an external device (or other IMD) does not output any pulses or any other signals that are detectable by the LP implanted within the patient, the external device (aka remote monitor, e.g., 702) (or other IMD, e.g., an ICM 104) need not include a transmitter (e.g., 732 in FIGS. 7A and 7B) that is specifically used for sending signals to an LP and/or other IMD configured to perform conductive communication.

The method summarized with reference to FIG. 9 can be disabled while the LP is in an actual communication session with an external programmer (e.g., 109), e.g., while the patient within which the LP is implanted is visiting a physician or other medical personnel. More specifically, in accordance with certain embodiments, the LP monitors for a programmer acknowledgement sequence of pulses within a programmer acknowledgement monitor window following each outputting by the LP of the advertisement sequence of pulses at instances of step 916, to thereby enable the LP to determine whether an external programmer is attempting to establish a communication session with the LP. If the LP detects the programmer acknowledgement sequence of pulses within a programmer acknowledgement monitor window, the LP cooperates with the external programmer (e.g., 109) to establish a communication session with the external programmer rather than outputting the notification sequence of pulses at step 920 within one or more notification transmission window(s) following the outputting of the advertisement sequence of pulses. In such an embodiment, the notification transmission window precedes, at least partially overlaps with, or follows the programmer acknowledgement monitor window.

In the method summarized with reference to FIG. 9, when the LP does not detect a programmer acknowledgement within a programmer acknowledgement monitor window that follows the LP outputting an advertising sequence of pulses, the LP outputs the notification sequence of pulses within one or more notification transmission window(s) following the output of the advertisement sequence of pulses only if the LP has recognized the presence of at least one notification condition (i.e., only if the answer to the determination at step 918 was Yes). In such an embodiment, the fact that the external device (or other IMD) does not receive a notification sequence of pulses is interpreted as there being no notification condition to report. In other words, no news is good news. In an alternative embodiment, a notification sequence is output by the LP when there are no actual notification conditions present, in which case the notification sequence would indicate that there are no notifications conditions to report. In such an embodiment the external device (or other IMD) expects to receive a specific notification message when there is no notification condition that exists. In other words, in this latter embodiment, good news is good news.

Active Remote Follow-Up

Figures 10A, 10B:
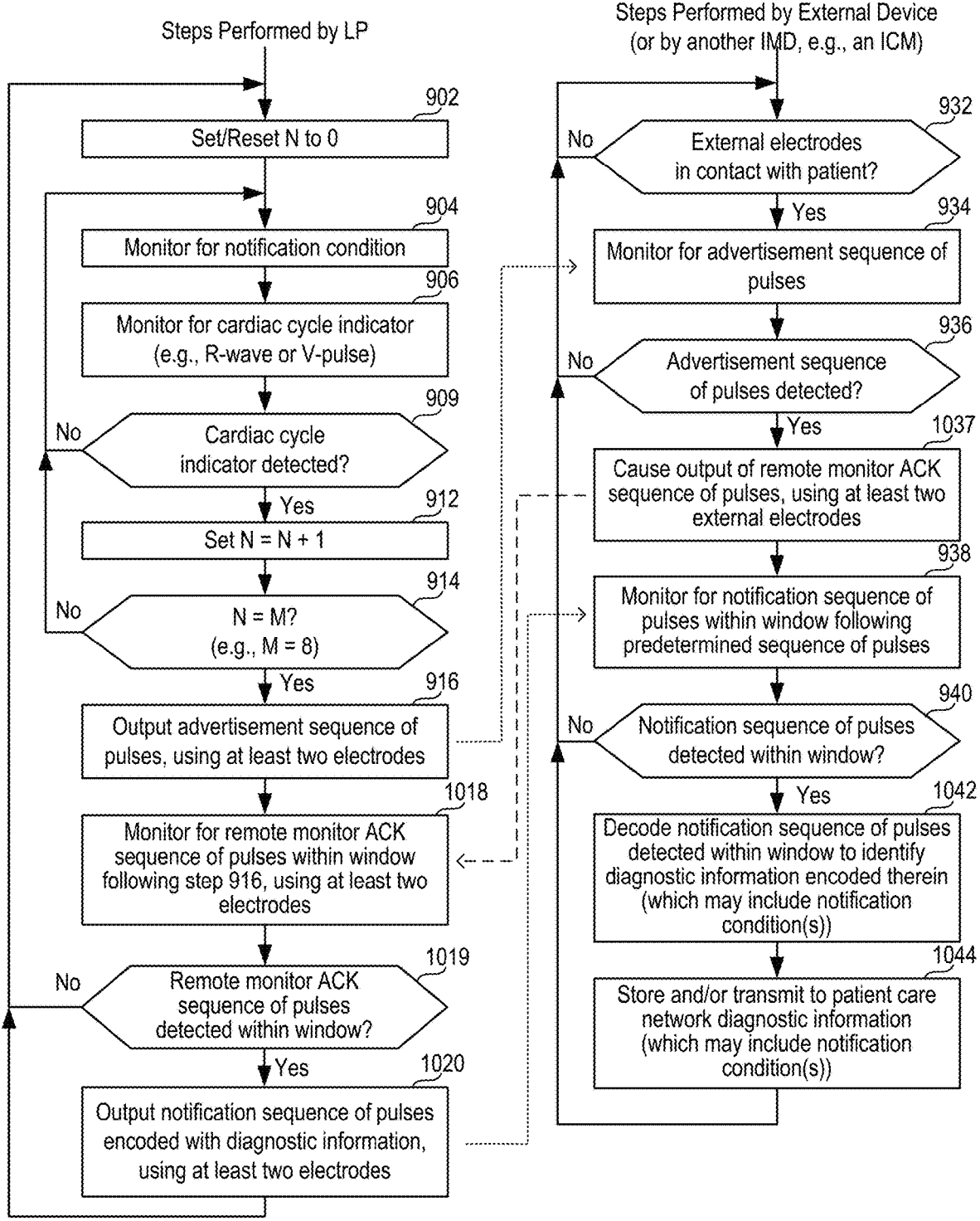
FIGS. 10A and 10B, which can be collectively referred to as FIG. 10, include a high level flow diagram that is used to summarize an "active" remote follow-up method for enabling an LP to provide diagnostic information to an external device (aka remote monitor) in accordance with certain embodiments of the present technology.

FIGS. 10A and 10B, which can be collectively referred to as FIG. 10, is a high level flow diagram that is used to summarize an "active" remote follow-up method for enabling an LP (e.g., 102a and/or 102b) to provide diagnostic information to an external device (aka remote monitor, e.g., 702). The steps shown in FIG. 10A are performed by an LP, e.g., 102a or 102b. The steps shown in FIG. 10B are performed by an external device (aka remote monitor, e.g., 702). The steps in FIG. 10A that are the same as those discussed above with reference to FIG. 9A are labeled the same, and need not be described in detail, since reference can be made to FIG. 9A for further details of such steps. The steps in FIG. 10B that are the same as those discussed above with reference to FIG. 9B are labeled the same, and need not be described in detail, since reference can be made to FIG. 9B for further details of such steps. In the "active" remote follow-up method, the external device (aka remote monitor) sends a remote monitor acknowledgement sequence of pulses in response to detecting an advertisement sequence of pulses, which acknowledgement sequence is detectable by the LP. Further, in the "active" remote follow-up method, the LP only outputs diagnostic information if it receives such a remote monitor acknowledgement sequence of pulses from an external device (aka remote monitor, e.g., 702), wherein the remote monitor acknowledgement sequence is different and distinguishable by the LP from a programmer acknowledgement sequence of pulses.

Referring to FIG. 10A, steps 902 through 916 are the same as steps 902 through 916 discussed above with reference to FIG. 9A. Following the outputting of the advertising sequence of pulses at step 916, the LP monitors for a remote monitor acknowledgement sequence of pulses at step 1018 within a window following the outputting of the advertising sequence at step 916. The notification sequence of pulses (which is encoded with diagnostic information associated with the LP and/or associated with the patient within which the LP is implanted) that is output at step 1020 can be referred to as an active out-of-session (OOS) alert, since it is sent while the LP is not in a communication session with an external programmer (e.g., 109). The term "active" indicates that the alert is sent in response to acknowledgement type of feedback from an external device. The advertisement sequence of pulses (output at step 916) and the notification sequence of pulses (output at step 1020) and/or information encoded therein are capable of being received by an external device (aka remote monitor, e.g., 702) that includes or is communicatively coupled to two or more external electrodes that are in contact with the patient's skin and used to receive conductive communication pulses from the LP.

At step 1019 there is a determination of whether the LP detects the remote monitor acknowledgement sequences of pulses within the window. If the answer to the determination at step 1019 is No, then flow returns to step 902, which is indicative of an external device (aka remote monitor) not being proximate to the patient with electrodes in contact with skin of the patient. If the answer to the determination at step 1019 is Yes, then the LP outputs a notification sequence of pulses, using at least two of its electrodes, e.g., within a notification transmission window following reception of the acknowledgement sequences of pulses. This notification sequence of pulses is encoded with diagnostic information associated with the LP and/or associated with the patient within which the LP is implanted. The advertisement sequence of pulses (output at step 916) and the notification sequence of pulses (output at step 1020) and/or information encoded therein are capable of being received by an external device (aka remote monitor, e.g., 702) that includes or is communicatively coupled to two or more external electrodes that are in contact with the patient's skin and used to receive conductive communication pulses from the LP.

Referring now to FIG. 10B, steps 932 through 936 are the same as steps 932 through 936 described above with reference to FIG. 9B. Following the advertisement sequence of pulses being detected at step 936, the external device (or other IMD) outputs a remote monitor acknowledgement (ACK) sequence of pulses. This can provide an indication to the LP that an external device is proximate to the patient with electrodes in contact with skin of the patient, or that another IMD is ready to receive information from the LP. Step 938 and 940 are the same as step 938 and 940 discussed above with reference to FIG. 9B. In response to the notification sequence of pulses being detected at step 940, at step 1042 (which is similar to step 942 discussed above with reference to FIG. 9B), the external device (or other IMD) decodes the notification sequence of pulsed detected within the window to identify diagnostic information, which includes one or more notification conditions encoded therein. At step 1044 (which is similar to step 944 discussed above with reference to FIG. 9B) the external device (or other IMD, e.g., an ICM 104) stores within its memory and/or transmits to a patient care network the diagnostic information it received from the LP. Following step 1044 flow returns to step 932.

In accordance with certain embodiments, following each instance of step 916, the LP monitors for a programmer acknowledgement sequence of pulses within a programmer acknowledgement monitor window (that follows each outputting by the LP of the advertisement sequence of pulses at an instance of step 916), to thereby enable the LP to determine whether an external programmer is attempting to establish a communication session with the LP. The programmer acknowledgement monitor window can precede the window within which a remote monitor ACK sequence of pulses is monitored for at instances of step 1018, or can completely or partially overlap with the window within which a remote monitor ACK sequence of pulses is monitored for at instances of step 1018, so long as the remote monitor ACK sequence of pulses is different than (and thus distinguishable from) the programmer acknowledgement sequence of pulses. In such an embodiment, if the LP does not detect the programmer acknowledgement sequence of pulses within the programmer acknowledgement monitor window, the LP may still detect an external device (aka remote monitor) acknowledgement sequence of pulses within the remote monitor ACK window following (or at least partially concurrent with) the programmer acknowledgement monitor window. The external device acknowledgement sequence of pulses can be transmitted by a remote monitor, or alternatively, by another IMD (e.g., an ICM) that acts as a communication bridge between the LP and the remote monitor. In response to the LP detecting the external device acknowledgement sequence of pulses within the external device acknowledgement monitor window, the LP outputs the notification sequence of pulses within one or more notification transmission window(s) following the outputting of the advertisement sequence of pulses, wherein the notification transmission window follows both the programmer acknowledgement monitor window and the external device acknowledgement monitor window.

In accordance with an embodiment, the LP outputs the notification sequence of pulses within one or more notification transmission window(s) following the outputting of the advertisement sequence of pulses only if the LP has recognized the presence of at least one notification condition and the LP has detected the external device acknowledgement sequence of pulses within the external device acknowledgement monitor window. In an alternative embodiment, a notification sequence is output by the LP when there are no actual notification conditions present, in which case the notification sequence would indicate that there are no notifications conditions to report.

In certain embodiments, in order to conserve energy, the LP limits how often the LP outputs the active OOS alert type of notification sequence of pulses within a specified period of time. In such embodiments, because the LP only sends the active OOS alert when it knows an external device (or another IMD, such as an ICM) is present and capable of receiving the active OOS alert, there is no need for the active OOS alert to be repetitively sent once per periodic based (e.g., once every eight cardiac cycles) if the LP has already sent an alert to an external device and the alert has not recently changed. For an example, the LP may limit outputting the active OOS alert type of notification sequence of pulse to once per hour, once every eight hours, once per day, or the like. In certain embodiments, the LP is prevented from repeated triggering of the active OOS alert type of notification sequence of pulses within a specified period (e.g., a one hour period, or a four hour period, or a day, etc.), in order to prevent intentional attacks or unintentional triggers that might lead to accelerated battery depletion. Another variant of above would be that only a small subset of critical OOS alerts/diagnostics (rather than a transmission of a full set of OOS diagnostics) would be repeated if the LP receives multiple triggers within a specified period.

Hybrid of Passive and Active Remote Follow-Up

Certain embodiments of the present technology are directed to a hybrid of the above described "passive" OOS alert and "active" OOS alert embodiments. In such a hybrid embodiment, which can also be referred to as a "hybrid" OOS alert embodiment, an LP (e.g., 102a and/or 102b) outputs a portion of the notification sequence of pulses irrespective of whether LP detects an external device acknowledgement sequence of pulses within the external device acknowledgment window, and thereafter, if the LP detects the external device acknowledgement sequence of pulses within the external device acknowledgment window, then the LP outputs a further portion of the notification sequence of pulses over one or more frames extending over one or more cardiac cycles. For example, where an LP has multiple packets (aka frames) of notification information that should be provided to a remote monitor, in a hybrid embodiment the LP can output a first packet (aka frame) of a notification sequence of pulses irrespective of whether LP detects an external device acknowledgement sequence of pulses within the external device acknowledgment window, and thereafter, if the LP detects the external device acknowledgement sequence of pulses within the external device acknowledgment window, then the LP will output one or more further packet(s) (aka frame(s)) of the notification sequence of pulses.

Waveforms, Timing Diagrams, and Packet Diagrams

Figure 11A:
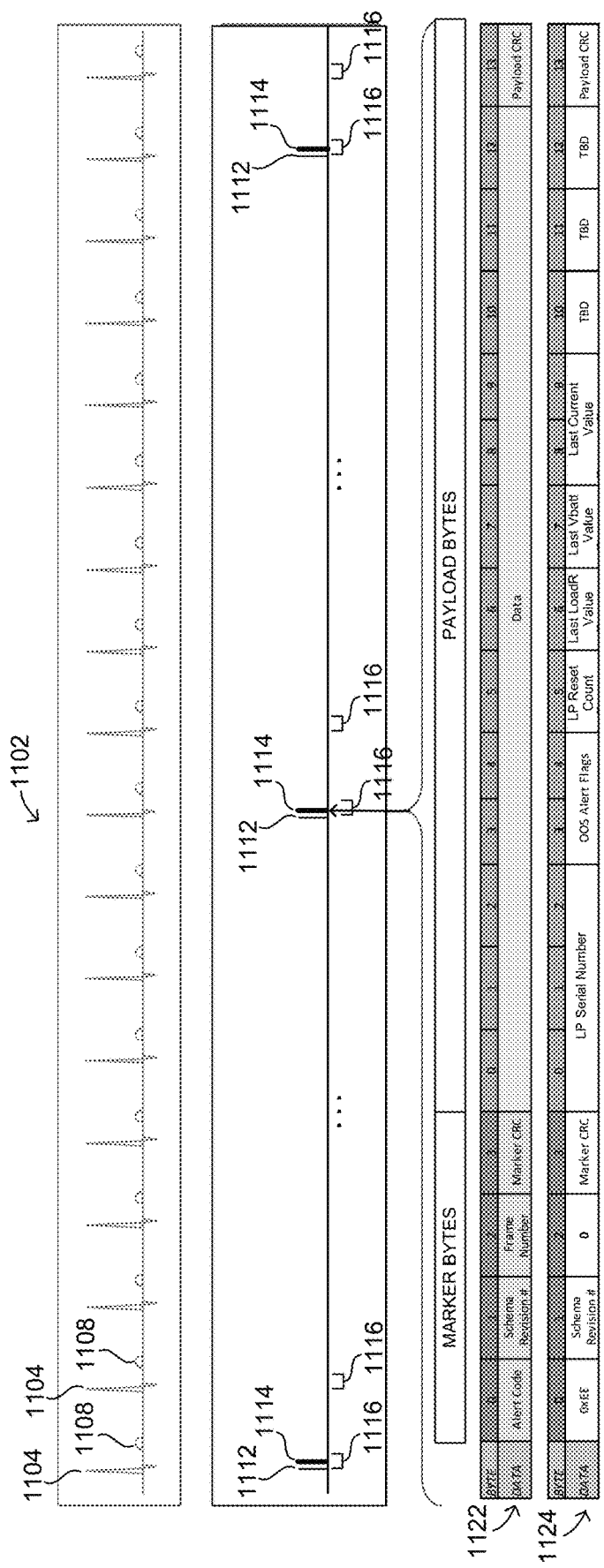
FIGS. 11A and 11B include waveforms, timing diagrams, and packet diagrams that are used to provide additional details, respectively, of the "passive" and "active" remote follow-up methods for enabling an LP to provide diagnostic information to an external device.
Figure 11B:
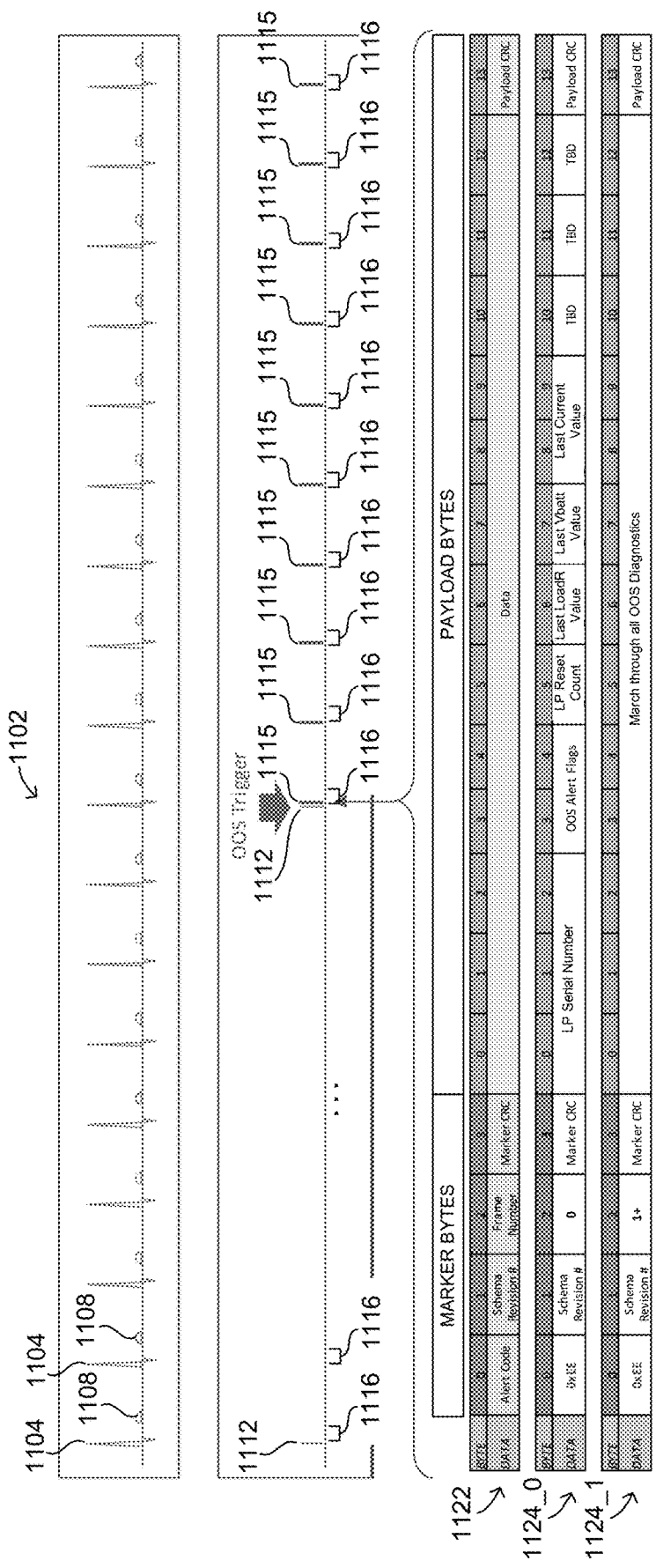

The waveforms, timing diagrams, and packet diagrams shown in and described with reference to FIGS. 11A and 11B provide additional details of the above described "passive" OOS alert and "active" OOS alert embodiments, respectively. Referring to FIG. 11A, which is used to provide additional details of the "passive" OOS alert embodiment introduced above with reference to FIGS. 9A and 9B, an example EGM signal 1102 is shown at the top of FIG. 11A, which includes QRS complexes 1104 and T-waves 1108. The QRS complexes 1104, or the R-waves thereof, are examples of cardiac cycle indicators that can be monitored for at instances of step 906 and detected at instances of step 908 by an LP (e.g., 102b) implanted in a ventricle, such as the right ventricle. The T-waves 1108 are examples of cardiac cycle indicators that can be monitored for at instances of step 906 and detected at instances of step 908 by an LP (e.g., 102a) implanted in an atrium, such as the right atrium. In the middle of FIG. 11A the thin vertical lines labeled 1112 correspond to the advertisement sequence of pulses (aka sniffs) that are output by an LP periodically, and more specifically in this example, every eight cardiac cycles at instances of step 916. In the middle of FIG. 11A the thick vertical lines labeled 1114 correspond to the notification sequence of pulses that are output within a window following each advertisement sequence of pulses 1112. The periods labeled 1116 correspond to cardiac refractory periods that follow intrinsic or paced ventricular activation. The length of the refractory periods can be programmed and can be, e.g., in the range of 100 to 500 ms long. As can be appreciated from FIG. 11A, the advertisement sequence of pulses and the notification sequence of pulses are output during cardiac refractory periods labeled 1116, so as to avoid the potential for the sequences of pulses inadvertently capturing cardiac tissue. Where an LP is an atrial LP, instead of a ventricular LP, the refractory periods would instead follow intrinsic or paced atrial activations.

Each notification sequence of pulses 1114 can provide a data packet, such as the data packet labeled 1122. In the example shown, each such data packet includes four marker bytes (0 through 3), and fourteen payload bytes (0 through 13), however more or less marker bytes and/or payload bytes than shown can be included in each packet 1122. The marker bytes, which can also be referred to as a header, can include an alert code byte, a schema revision number byte, a frame number byte, and a marker cyclic redundancy check (CRC) value. The alert code byte can provide an indication of the type of notification (aka alert) that is being provided. The scheme revision number byte can provide an indication of a protocol being used by the LP. The frame number byte can provide an indication of a frame number, which would be useful in situations where multiple frames are required for an LP to output all of its notification information, which can also be referred to as diagnostic information. The marker CRC value can be used for error detection and correction of the marker. The last byte of the payload bytes can include a payload CRC value that can be used for error detection and correction of the payload.

The data packet labeled 1124 provides example details of the bytes included in the payload bytes. In this example, the first three bytes include the serial number of the LP. The next two bytes (and thus, sixteen bits) include OOS alert flags, which can indicate for each of sixteen possible types of notifications, whether or not the type of notification is being provided, whereby a "0" flag corresponds to a type of notification (e.g., RRT threshold reached) not being provided, and a "1" flag corresponds to the type of notification being provided. Other bytes within the payload bytes can include a reset count value, a load measurement (e.g., Last LoadR Value), a battery measurement (e.g., Last Vbatt Value), a current demand measurement (e.g., Last Current Value), and/or the like. These are just a few examples of the types of information that can be included within the payload bytes.

Reference is now made to FIG. 11B, which is used to provide additional details of the above described "active" 00S alert embodiment introduced above with reference to FIGS. 10A and 10B. Referring to FIG. 11B, an example EGM signal 1102 is shown at the top, which is the same as the EGM signal 1102 shown in FIG. 11A, and thus need not be described again. In the middle of FIG. 11B the thin vertical lines labeled 1112 correspond to the advertisement sequence of pulses (aka sniffs) that are output by an LP periodically, and more specifically in this example, every eight cardiac cycles at instances of step 916. In the middle of FIG. 11B the thick vertical lines labeled 1115 correspond to the notification sequence of pulses. In this embodiment, the notification sequence of pulses is only output by an LP in response to the LP receiving a remote monitor ACK sequence of pulses from an external device (aka remote monitor, e.g., 702) within a window following the LP outputting an advertisement sequence of pulses (aka sniff). The thick arrow in the middle labeled "OOS Trigger" indicates a point in time at which the LP receives such a remote monitor ACK sequence of pulses at instances of steps 1018, 1019. Thereafter, the LP outputs multiple packets (aka frames) of notification information, wherein each frame includes a different frame number with its frame number byte within the marker bytes. While only two packets (labeled 1124_0 and 1124_1) are represented, additional packets are also sent at additional points in time labeled 1115. While only one notification sequence of pulses 1115 is shown as being transmitted in a single cardiac cycle, more than one notification sequence of pulse 1115 can be transmitted during a single cardiac cycle, and more specifically, during a single cardiac refractory period of a cardiac cycle. The contents of each of the packets 1124 are the same or similar to those labeled the same in FIG. 11A, and thus need not be described again.

Improving Reception of Conductive Communication Signals by Remote Monitor

As noted above in the discussion of FIGS. 7A, 7B, 8A, and 8B, in certain embodiments a remote monitor 702 (aka external device) can have three electrodes 715 in or on the housing of the remote monitor 702 or communicatively coupled thereto. Referring back to FIGS. 8A and 8B, a patient can touch the electrode 715a using one or more digits of their left hand, and can touch the electrode 715b using one or more digits on their right hand. A third electrode 715c can be located, e.g., on the backside of the housing 812 or 814. A patient can touch such a third electrode 715c to a portion (e.g., upper thigh) of one of their legs. In certain embodiments, summarized with reference to the high level flow diagrams of FIGS. 12 and 13, the third electrode 715c can be used to selectively improve the remote monitor's reception of conductive communication signals (e.g., sequences of pulses) that are output by an LP. The steps described with reference to FIGS. 12 and 13 are performed by an external device (aka remote monitor, e.g., 702) while the external device is attempting to receive conductive communication signals, which include sequences of pulses, from an implanted LP (e.g., 102*a* or 102*b*).

Figure 12:
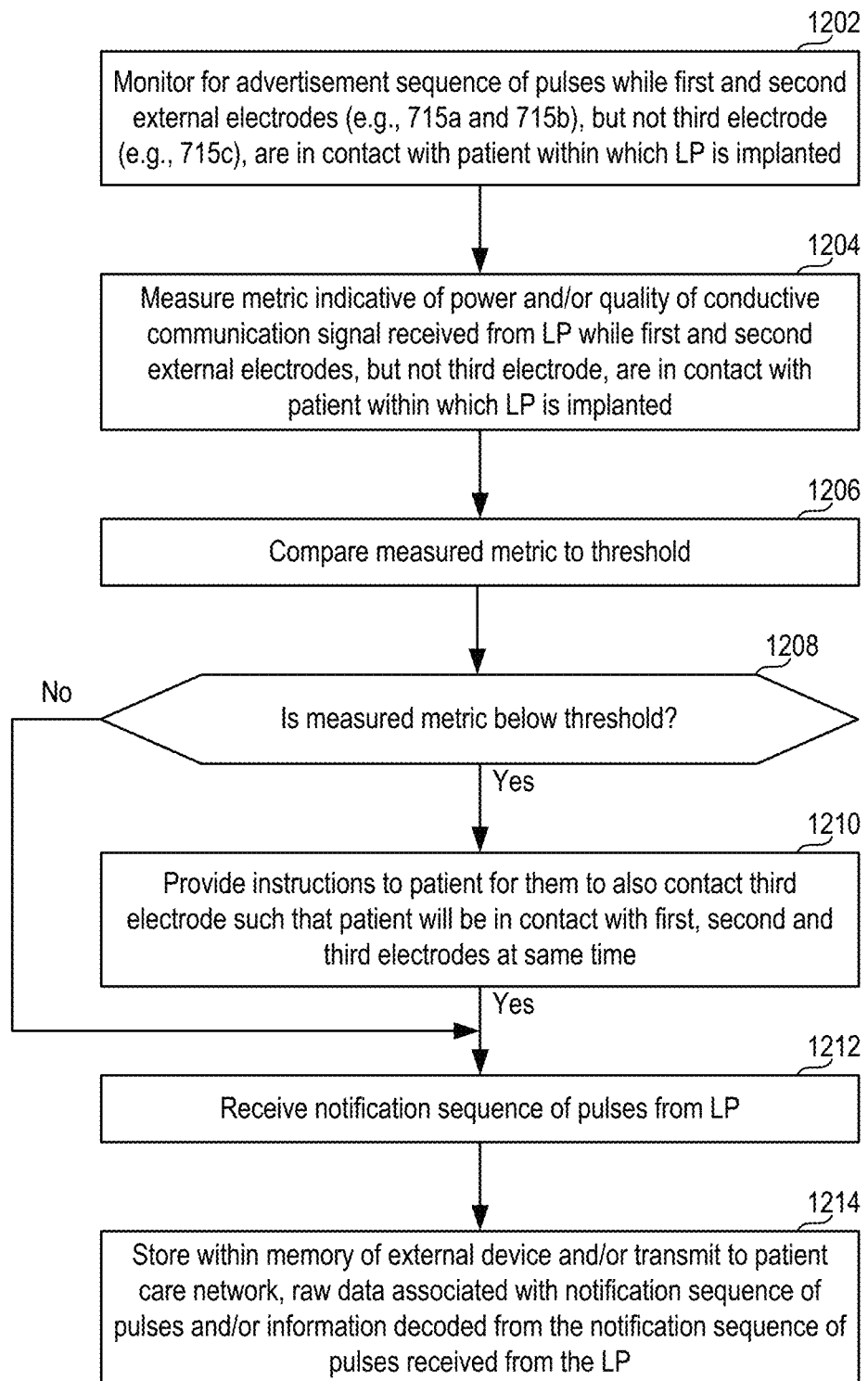
FIG. 12 is a high level flow diagram that is used to summarize a method in which an external device can selectively instruct a patient, whom is already in contact with two external electrodes, to also contact a third external electrode in order to improve the reception of conductive communication signals from an implanted LP.
Figure 13:
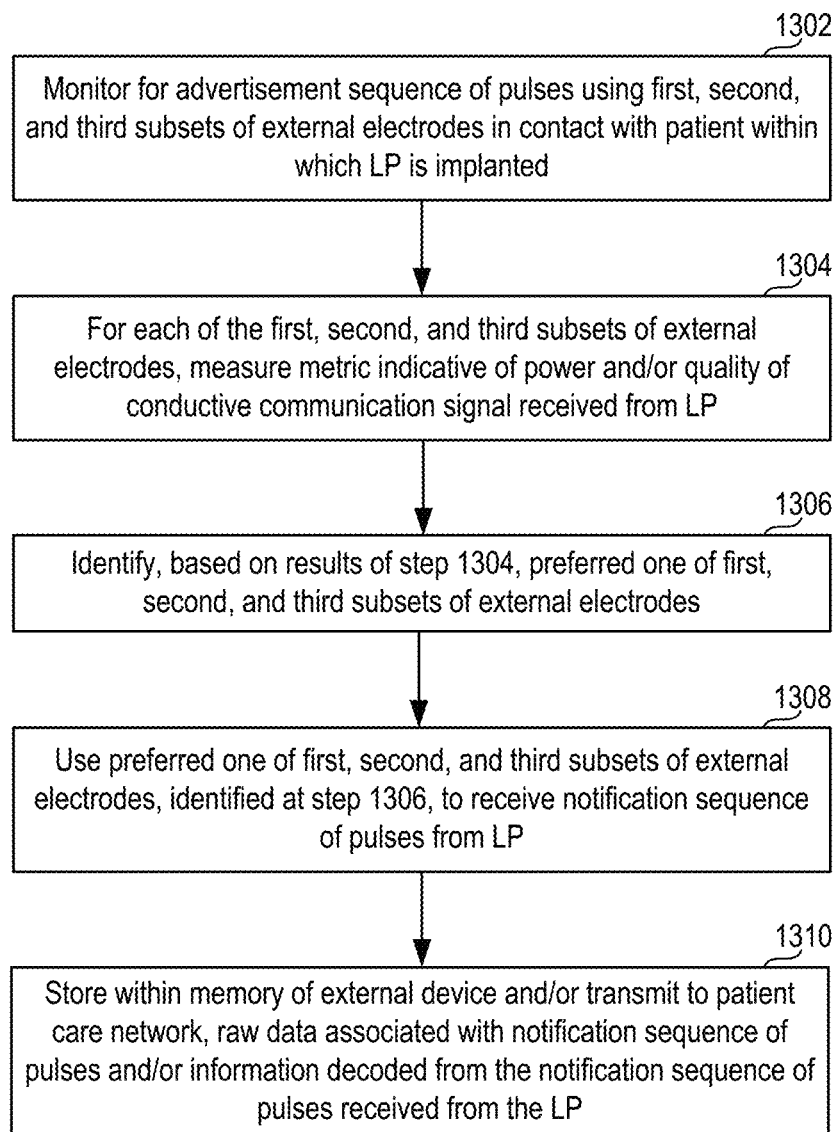
FIG. 13 is a high level flow diagram that is used to summarize a method in which an external device can select a preferred sensing vector, from among three or more external electrodes, for receiving conductive communication signals from an implanted LP.

Referring to the high level flow diagram of FIG. 12, step 1202 involves monitoring for the advertisement sequence of pulses while the first and second external electrodes (e.g., 715*a* and 715*b*), but not the third electrode (e.g., 715*c*), are in contact with the patient within which the LP is implanted. More generally, step 1202 involves the external device using two external electrodes to monitor for a conductive communication signal from an implanted LP.

Step 1204 involves the external device measuring a metric indicative of power and/or quality of a conductive communication signal received from the LP while the first and second external electrodes, but not the third electrode, are in contact with the patient within which the LP is implanted. In specific embodiments, it is presumed that the conductive communication signal includes at least one instance of the advertisement sequence of pulses. At step 1206, the metric measured at step 1204 is compared to a corresponding threshold. At step 1208 there is a determination of whether the measured metric is below the corresponding threshold. A metric of quality can, e.g., be based on how similar the morphology of one or more received pulses (e.g., in the advertisement sequence of pulses) are to an expected morphology. A metric of quality can alternatively be indicative of a signal to noise ratio, e.g., which metric can be a ratio of an amplitude (or power, etc.) of received pulses relative to an amplitude (or power, etc.) of received noise. Additional and/or alternative ways to determine a metric of quality are also possible and within the scope of the embodiments described herein. A metric of power can, e.g., be a measure of the amplitude of received pulses (e.g., in the advertisement sequence of pulses). Additional and/or alternative ways to determine a metric of power are also possible and within the scope of the embodiments described herein. More than one metric of quality and/or power can be measured and be combined into a single metric (e.g., by determining an average, or weighted average) that is compared to a corresponding threshold. Other variations are also possible and within the scope of the embodiments described herein.

Still referring to FIG. 12, if the answer to the determination at step 1208 is No, then flow goes to step 1212. If the answer to the determination at step 1208 is Yes, then flow goes to step 1210 before going to step 1212. At step 1210 the external device provides instructions (e.g., via a display and/or audio speaker) to the patient, instructing the patient to also contact the third electrode (e.g., 715*c*, e.g., on the backside of the external device), so that the patient is in contact with the first, second, and third electrodes (e.g., 715*a*, 715*b*, and 715*c*) at the same time. The third electrode can, for example, be placed on contact with a patient's left or right leg, left or right hip, or abdomen, etc.

At step 1212 the external device receives a notification sequence from the LP, and at step 1214 the external device stores within memory of the external device and/or transmits to a patient care network, raw data associated with the notification sequence of pulses and/or information decoded from the notification sequence of pulses received from the LP. As part of step 1212, the external device can couple two of the three electrodes to one another to essentially increase the size of the electrode. Alternatively, as part of step 1212, the external device can perform the steps described below with reference to FIG. 13 to identify a preferred sensing vector and receive the notification sequence, or more generally a conductive communication signal, from the implanted LP using the identified preferred sensing vector. In an alternative embodiment, the patient can be in contact with first, second, and third electrodes from the start, but initially (at steps 1202, 1204, 1206, and 1208) only the first and second electrodes are used to monitor for an advertisement sequence of pulses (e.g., by using an internal switch to disconnect the third electrode from sensing circuitry), and then, if the answer to the determination at step 1208 is Yes (i.e., if the measured metric is below the threshold), then the third electrode can also (or in place of one of the first and second electrodes) be connected to the sensing circuitry at an alternative step 1210. Other variations are also possible while being within the sprit and scope of the embodiments described herein.

Referring now to the high level flow diagram of FIG. 13, step 1302 involves the external device monitoring for the advertisement sequence of pulses using first, second, and third subsets of the external electrodes, the first subset including the first and second external electrodes, the second subset including the first and third external electrodes, and the third subset including the second and third external electrodes. More generally, at step 1302 the external device monitors for conductive communication pulses (output by an implanted LP) using a plurality of different sensing vectors.

At step 1304, the external device measures for each subset of the external electrodes, of the first, second, and third subsets, a respective metric indicative of power and/or quality of a communication signal received from the LP using the subset of electrodes. More generally, at step 1302 the external device determines a metric of power and/or quality for each of the plurality of different sensing vectors.

At step 1306, the external device identifies, based on the results of step 1304, a preferred one of the first, second, and third subsets of the external electrodes. More generally, at step 1306 the external device selects a preferred sensing vector, based on the results of step 1304.

At step 1308, the external device uses the preferred one of the first, second, and third subsets of the external electrodes, which was identified at step 1306, to receive the notification sequence of pulses from the LP. More generally, at step 1308 the external device uses the identified preferred sensing vector to receive one or more conductive communication signals from an LP.

At step 1310, the external device stores within memory of the external device and/or transmits to a patient care network, raw data associated with the notification sequence of pulses and/or information decoded from the notification sequence of pulses received from the LP using the preferred one of the first, second, and third subsets of the external electrodes. More generally, at step 1310 the external device stores and/or forwards data it obtained from one or more conductive communication signals received from an implanted LP using the identified preferred sensing vector.

External Device (Non-Programmer) for Remote Follow-Up Communication with LP(s)

Figure 14:
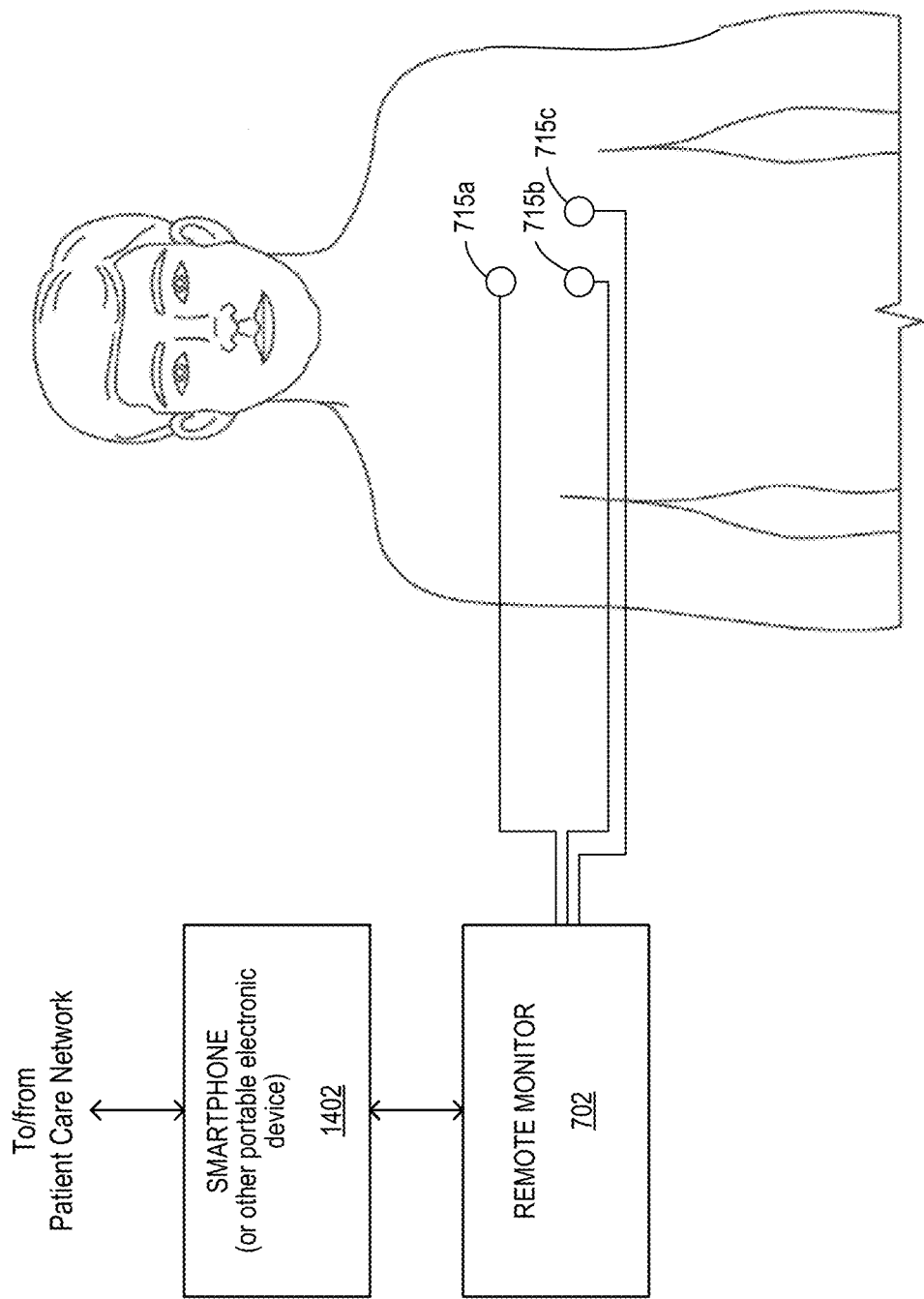
FIGS. 14-16 show details of a remote monitor in accordance with other embodiments of the present technology.
Figure 15:
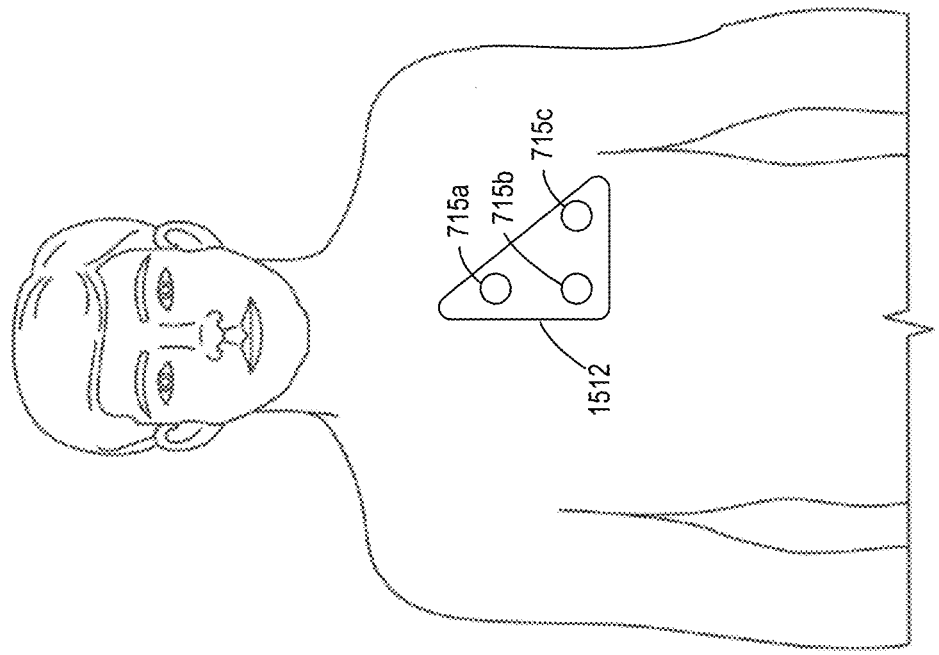
Figure 15:
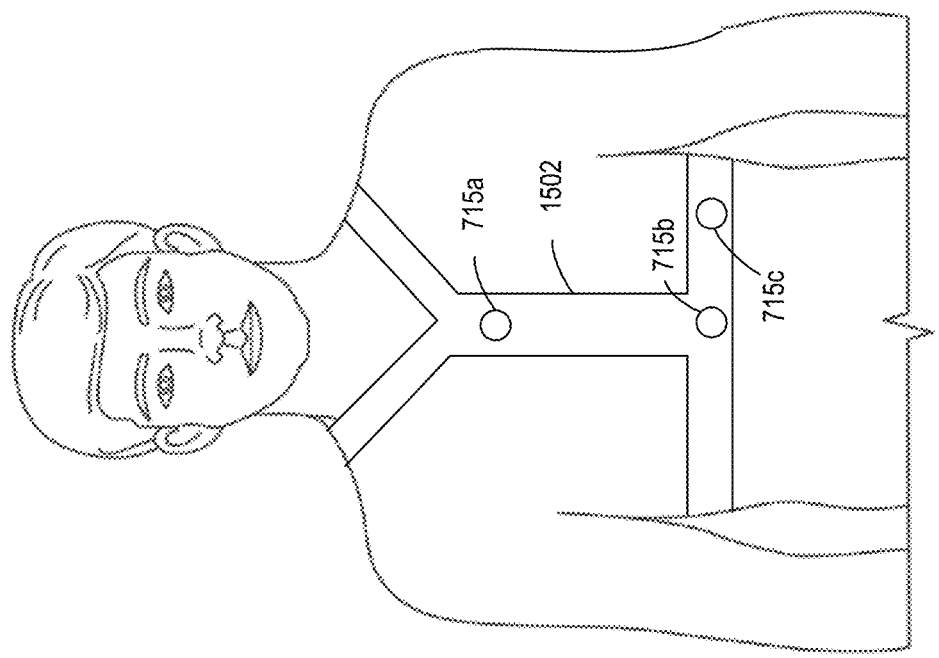
Figure 16:
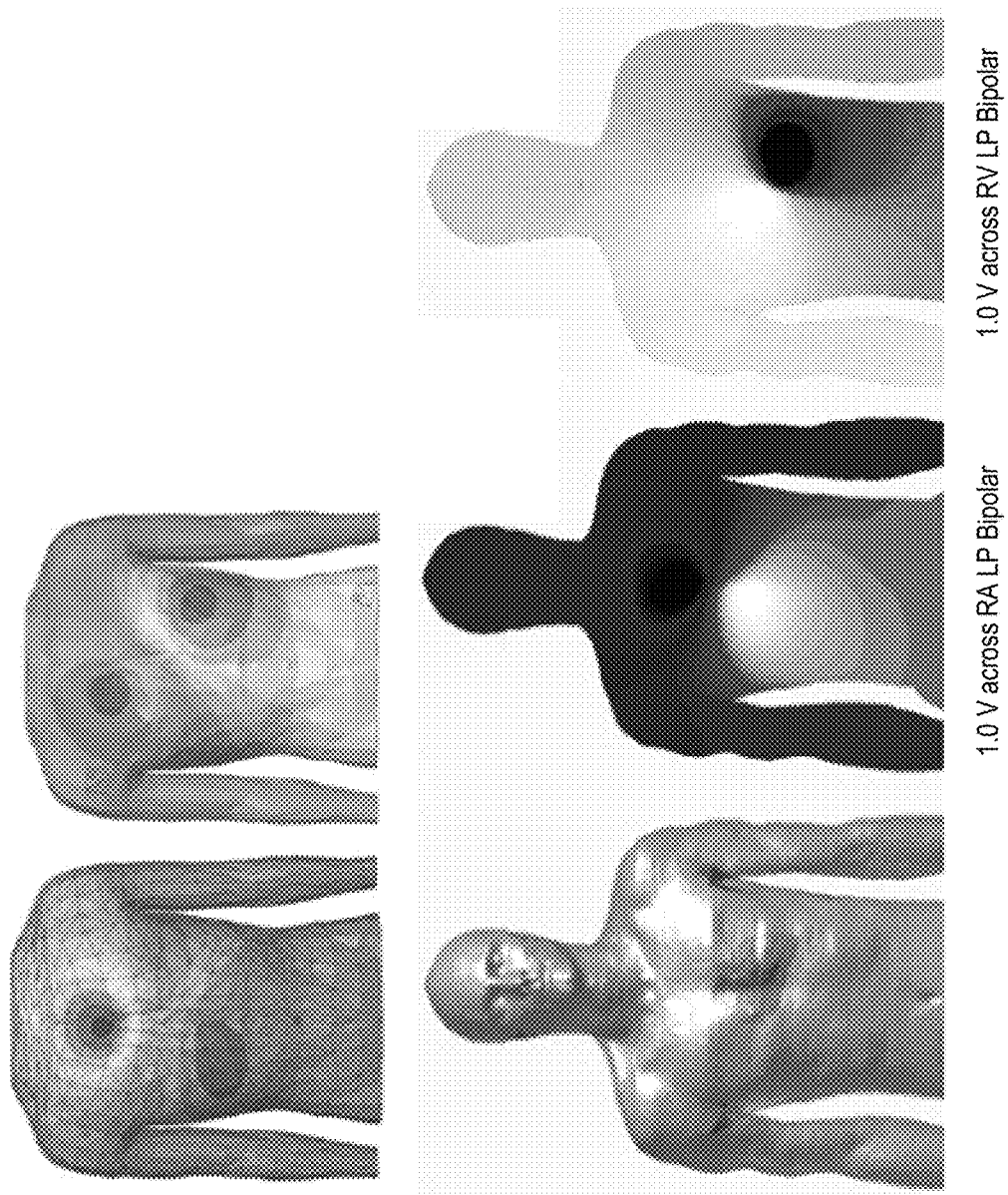

FIGS. 14-16 show details of a remote monitor in accordance with other embodiments of the present technology. In such an embodiment, a remote follow-up device or system includes three electrodes 715*a*, 715*b*, 715*c* that are connected to a remote monitor device 702. The remote monitor device 702 can communicate directly with a patient care network if the remote minor device 702 has appropriate communication capabilities for doing so. Alternatively, the remote monitor device 702 can be communicatively coupled to a smartphone 1402 via a wired or wireless connection, and the remote monitor device 702 can utilize the communication capabilities of the smartphone 1402 (or tablet computing device or other portable electronic device with communication capabilities) to communicate with the patient care network. Other variations are also possible and within the scope of the embodiments described herein. The electrodes 715a, 715b, and 715c can be separately attachable to a patient's chest, as shown in FIG. 14, or they can be incorporated into a wearable Y vest (1502 in FIG. 15) or stick-on patch (1512 in FIG. 5). Either way, the three electrodes 715a, 715b, 715c can provide for a pair of orthogonal sensing vectors.

A software application can provide for a connection through the internet to a patient care network, such as the Merlin.net system, where a physician can monitor key parameters of one or more LPs, therapy delivery and patient status. The hardware design for this system could utilize a smartphone (or tablet computing device or other portable electronic device) as both a power source and controller, with the monitor device providing the two-way communication (sensing and pulses) and hardware interface to the electrodes. In certain embodiment, the electrodes could utilize single use stick-on electrodes and then re-usable clips to connect to the device. The overall system can be used to compensate for the minimal on-board data storage included in LPs by obtaining EGM recordings as needed while worn. A stick-on patch 1512 or wearable Y vest 1502 can provide for conductive communication/telemetry through a programmer-to-implant (p2i) protocol, or the like. Since the electrodes can be attached to a patient for an extended period of time, without requiring constant attention or cooperation from the patient, the electrodes can allow for slower speed transmission of data, and can provide for real time recording of extended EGM data that would require too much memory to store within an LP's memory.

Based on simulations in human thorax models, electrical potential distribution on body surface are shown in FIG. 16 with LPs in the RA and RV chambers. The potential map on body surface would guide telemetry electrode placement. For p2i telemetry pulses from LP in RA in FIG. 16A, the "eye balls" are where minimum and maximum potential locations are vertical on sternum pointing to the left. When p2i pulses are from the LP in RV chamber, as shown in FIG. 16B, the "eye balls" are about 45 degree from upper left down to the right anterior chest. In certain methods, orthogonal X-Y pairs of electrodes can be used to measure p2i telemetry conductive pulses Vx and Vy so that V=sqrt(Vx^2+Vy^2). This approach can provide for optimal vectors for either RA LP pulses or RV LP pulses.

The embodiments described with reference to FIGS. 14-16 can be used with the embodiments summarized with reference to FIGS. 9A-13, and/or with other ways of performing remote monitoring.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:
   the LP monitoring for a presence of one or more notification conditions associated with the LP and/or associated with a patient within which the LP is implanted;
   the LP periodically outputting an advertisement sequence of pulses, using at least two of the two or more implantable electrodes of the LP, irrespective of whether the LP recognizes the presence of at least one said notification condition; and
   the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;
   wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP; and
   wherein the external device does not output any pulses or other signals that are detectable by the LP implanted within the patient, and thus, the LP is unaware of whether any instances of the advertisement sequence of pulses and the notification sequence of pulses that the LP outputs are received by the external device.

2. The method of claim 1, wherein:
the LP outputs the advertisement sequence of pulses, using at least two of the two or more implantable electrodes, during a cardiac refractory period once every Nth cardiac cycle of the patient within which the LP is implanted, wherein N is an integer that is greater than 1.

3. The method of claim 1, wherein:
the one or more notification conditions that the LP monitors for includes at least one notification condition associated with the LP and/or at least one notification condition associated with the patient within which the LP is implanted;
the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and
the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

4. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:
the LP monitoring for a presence of one or more notification conditions associated with the LP and/or associated with a patient within which the LP is implanted;
the LP periodically outputting an advertisement sequence of pulses, using at least two of the two or more implantable electrodes of the LP, irrespective of whether the LP recognizes the presence of at least one said notification condition;
the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;
the LP monitoring for a programmer acknowledgement sequence of pulses within a programmer acknowledgement monitor window following each outputting by the LP of the advertisement sequence of pulses, to thereby enable the LP to determine whether an external programmer is attempting to establish a communication session with the LP; and
in response to the LP detecting the programmer acknowledgement sequence of pulses within the programmer acknowledgement monitor window, the LP cooperating with the external programmer to establish a communication session with the external programmer;
wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP; and
wherein during a said communication session with the external programmer, the LP abstains from outputting the notification sequence of pulses that is capable of being received by a said external device that is incapable of programming the LP or by another IMD.

5. The method of claim 4, wherein:
the LP outputs the advertisement sequence of pulses, using at least two of the two or more implantable electrodes, during a cardiac refractory period once every Nth cardiac cycle of the patient within which the LP is implanted, wherein N is an integer that is greater than 1.

6. The method of claim 4, wherein:
the one or more notification conditions that the LP monitors for includes at least one notification condition associated with the LP and/or at least one notification condition associated with the patient within which the LP is implanted;
the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and
the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

7. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:
the LP monitoring for a presence of one or more notification conditions associated with the LP and/or associated with a patient within which the LP is implanted;
the LP periodically outputting an advertisement sequence of pulses, using at least two of the two or more implantable electrodes of the LP, irrespective of whether the LP recognizes the presence of at least one said notification condition; and
the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;

the LP monitoring for a programmer acknowledgement sequence of pulses within a programmer acknowledgement monitor window following each outputting by the LP of the advertisement sequence of pulses, to thereby enable the LP to determine whether an external programmer is attempting to establish a communication session with the LP; and in response to the LP not detecting the programmer acknowledgement sequence of pulses within the programmer acknowledgement monitor window, the LP outputting the notification sequence of pulses within one or more said notification transmission window following the outputting of the advertisement sequence of pulses;

wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP.

8. The method of claim 7, wherein:
when the LP does not detect a said programmer acknowledgement within a said programmer acknowledgement monitor window that follows the LP outputting a said advertising sequence of pulses, the LP outputs the notification sequence of pulses within one or more said notification transmission window following the outputting of the advertisement sequence of pulses only if the LP has recognized the presence of at least one said notification condition.

9. The method of claim 7, wherein:
the LP outputs the advertisement sequence of pulses, using at least two of the two or more implantable electrodes, during a cardiac refractory period once every Nth cardiac cycle of the patient within which the LP is implanted, wherein N is an integer that is greater than 1.

10. The method of claim 7, wherein:
the one or more notification conditions that the LP monitors for includes at least one notification condition associated with the LP and/or at least one notification condition associated with the patient within which the LP is implanted;

the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

11. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:

the LP monitoring for a presence of one or more notification conditions associated with the LP and/or associated with a patient within which the LP is implanted;

the LP periodically outputting an advertisement sequence of pulses, using at least two of the two or more implantable electrodes of the LP, irrespective of whether the LP recognizes the presence of at least one said notification condition;

the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;

wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP;

the external device or other IMD monitoring for the advertisement sequence of pulses;

the external device or other IMD detecting the advertisement sequence of pulses and in response thereto the external device monitoring for a said notification sequence of pulses within a respective notification monitor window following the said advertisement sequence of pulses that was detected by the external device or other IMD; and the external device or other IMD detecting a said notification sequence of pulses within a said respective notification monitor window following the said advertisement sequence of pulses that was detected by the external device or other IMD, and in response thereto, the external device or other IMD storing and/or transmitting to a patient care network, raw data associated with the notification sequence of pulses and/or information decoded from the notification sequence of pulses.

12. The method of claim 11, wherein:
the LP outputs the advertisement sequence of pulses, using at least two of the two or more implantable electrodes, during a cardiac refractory period once every Nth cardiac cycle of the patient within which the LP is implanted, wherein N is an integer that is greater than 1.

13. The method of claim 11, wherein:
the one or more notification conditions that the LP monitors for includes at least one notification condition associated with the LP and/or at least one notification condition associated with the patient within which the LP is implanted;

the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

14. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:

the LP monitoring for a presence of one or more notification conditions associated with the LP and/or associated with a patient within which the LP is implanted;

the LP periodically outputting an advertisement sequence of pulses, using at least two of the two or more implantable electrodes of the LP, irrespective of whether the LP recognizes the presence of at least one said notification condition;

the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;

wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP;

the external device or other IMD monitoring for the advertisement sequence of pulses;

the external device or other IMD detecting the advertisement sequence of pulses and in response thereto the external device or other IMD monitoring for a said notification sequence of pulses within a respective notification monitor window following the said advertisement sequence of pulses that was detected by the external device or other IMD; and the external device or other IMD not detecting a said notification sequence of pulses within the respective notification monitor window following the said advertisement sequence of pulses that was detected by the external device or other IMD, and in response thereto, the external device or other IMD storing and/or transmitting to a patient care network an indication that no notification condition was reported by the LP.

15. The method of claim 14, wherein:
the LP outputs the advertisement sequence of pulses, using at least two of the two or more implantable electrodes, during a cardiac refractory period once every Nth cardiac cycle of the patient within which the LP is implanted, wherein N is an integer that is greater than 1.

16. The method of claim 14, wherein:
the one or more notification conditions that the LP monitors for includes at least one notification condition associated with the LP and/or at least one notification condition associated with the patient within which the LP is implanted;

the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

17. A method for providing an implantable leadless pacemaker (LP) with a remote follow-up capability whereby the LP can provide diagnostic information to an external device that is incapable of programming the LP, wherein the LP includes two or more implantable electrodes used to output both pacing pulses and conductive communication pulses, the method comprising:

the LP monitoring for a presence of one or more notification conditions associated with the LP and/or associated with a patient within which the LP is implanted;

the LP periodically outputting an advertisement sequence of pulses, using at least two of the two or more implantable electrodes of the LP, irrespective of whether the LP recognizes the presence of at least one said notification condition;

the LP recognizing the presence of at least one said notification condition, and based thereon, the LP also outputting a notification sequence of pulses, using at least two of the two or more implantable electrodes of the LP, within one or more notification transmission windows following the outputting of the advertisement sequence of pulses, the notification sequence of pulses encoded with diagnostic information associated with the LP and/or associated with the patient within which the LP is implanted;

wherein the advertisement sequence of pulses and the notification sequence of pulses and/or information encoded therein are capable of being received by an external device that includes or is communicatively coupled to two or more external electrodes used to receive conductive communication pulses from the LP or by another implantable medical device (IMD) that includes two or more electrodes used to receive conductive communication pulses from the LP;

wherein the one or more notification conditions that the LP monitors for includes at least one notification condition associated with the LP and/or at least one notification condition associated with the patient within which the LP is implanted;

wherein the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and wherein the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

18. The method of claim 17, wherein:

the LP outputs the advertisement sequence of pulses, using at least two of the two or more implantable electrodes, during a cardiac refractory period once every Nth cardiac cycle of the patient within which the LP is implanted, wherein N is an integer that is greater than 1.

19. The method of claim 17, wherein:

the one or more notification conditions that the LP monitors for includes at least one notification condition associated with the LP and/or at least one notification condition associated with the patient within which the LP is implanted;

the at least one notification condition associated with the LP comprises one or more of a recommended replacement time (RRT) condition, a device reset condition, an end of service (EOS) condition, a high current condition, a memory region full condition, a memory corruption condition, or a poor conductive communication condition; and the at least one notification condition associated with the patient comprises one or more of an arrhythmia detection, a non-cardiac physiological condition detection, an increased pacing burden detection, an automatic mode switching (AMS) detection, a pacemaker mediated tachycardia (PMT) detection, or a premature ventricular contraction (PVC) detection.

* * * * *